US010238622B2

(12) United States Patent
Mueller et al.

(10) Patent No.: US 10,238,622 B2
(45) Date of Patent: Mar. 26, 2019

(54) METHODS OF TREATING AND PREVENTING/REDUCING THE LIKELIHOOD OF MESIAL TEMPORAL LOBE EPILEPSY (TLE)

(76) Inventors: Wolfgang S. Mueller, Albuquerque, NM (US); John A. Connor, Albuquerque, NM (US); Steven Peterson, Corpus Christi, TX (US); Denis Bragin, Albuquerque, NM (US)

(*) Notice: Subject to any disclaimer, the term of this patent is extended or adjusted under 35 U.S.C. 154(b) by 1076 days.

(21) Appl. No.: 13/380,921

(22) PCT Filed: Jul. 23, 2010

(86) PCT No.: PCT/US2010/043063
§ 371 (c)(1),
(2), (4) Date: Jan. 24, 2012

(87) PCT Pub. No.: WO2011/011692
PCT Pub. Date: Jan. 27, 2011

(65) Prior Publication Data
US 2012/0115919 A1    May 10, 2012

Related U.S. Application Data

(60) Provisional application No. 61/271,714, filed on Jul. 24, 2009, provisional application No. 61/281,095, filed on Nov. 12, 2009.

(51) Int. Cl.
*A61K 31/34* (2006.01)
*A61K 31/40* (2006.01)
*A61K 31/41* (2006.01)
*A61K 31/44* (2006.01)
*A61K 45/06* (2006.01)

(52) U.S. Cl.
CPC .............. *A61K 31/34* (2013.01); *A61K 31/40* (2013.01); *A61K 31/41* (2013.01); *A61K 31/44* (2013.01); *A61K 45/06* (2013.01)

(58) Field of Classification Search
CPC ........ A61K 31/34; A61K 31/40; A61K 31/41; A61K 31/44; A61K 45/06
USPC ....................................................... 514/114
See application file for complete search history.

(56) References Cited

U.S. PATENT DOCUMENTS

| 2005/0075282 | A1 | 4/2005 | Coulter |
| 2006/0025387 | A1* | 2/2006 | Hochman ............ 514/165 |
| 2007/0043034 | A1 | 2/2007 | Staley |
| 2009/0176865 | A1 | 7/2009 | Breslav |

FOREIGN PATENT DOCUMENTS

WO    WO 2010085352 A2 *    7/2010    ......... A61K 31/4355

OTHER PUBLICATIONS

Loscher, Epilepsia, 2007, Blackwell Publishing, vol. 48, suppl., 8, pp. 74-77.*
DeFelipe et. al., Seminars in Ultrasound CT and MRI, 2007, Elsevier, vol. 28, pp. 404-415.*
Zak et. al., Annals of Neurology, 1994, American Neurological Association, vol. 36, No. 1, pp. 113-114.*
Aickin, C.C., Deisz, R.A. & Lux, H.D. (1984) Mechanisms of chloride transport in crayfish stretch receptor neurones and guinea pig vas deferens: implications for inhibition mediated by GABA. Neurosci Lett, 47, 239-244.
Andre, V., Dube, C., Francois, J., Leroy, C., Rigoulot, M.A., Roch, C., Namer, I.J. & Nehlig, A. (2007) Pathogenesis and pharmacology of epilepsy in the lithium-pilocarpine model. Epilepsia, 48 Suppl 5, 41-47.
Annegers, J.F., Grabow, J.D., Groover, R.V., Laws, E.R., Jr., Elveback, L.R. & Kurland, L.T. (1980) Seizures after head trauma: a population study. Neurology, 30, 683-689.
Arzimanoglou, A., Hirsch, E., Nehlig, A., Castelnau, P., Gressens, P. & Pereira de Vasconcelos, A. (2002) Epilepsy and neuroprotection: an illustrated review. Epileptic Disord, 4, 173-182.
Beck, J., Lenart, B., Kintner, D.B. & Sun, D. (2003) Na—K—Cl cotransporter contributes to glutamate-mediated excitotoxicity. J Neurosci, 23, 5061-5068.
Ben-Ari, Y., Gaiarsa, J.L., Tyzio, R. & Khazipov, R. (2007) GABA: a pioneer transmitter that excites immature neurons and generates primitive oscillations. Physiol Rev, 87, 1215-1284.
Bernard, C., Anderson, A., Becker, A., Poolos, N.P., Beck, H. & Johnston, D. (2004) Acquired dendritic channelopathy in temporal lobe epilepsy. Science, 305, 532-535.
Bormann, J., Hamill, O.P. & Sakmann, B. (1987) Mechanism of anion permeation through channels gated by glycine and gamma-aminobutyric acid in mouse cultured spinal neurones. J Physiol, 385, 243-286.
Brandt, C., Nozadze, M., Heuchert, N., Rattka, M. & Loscher, W. (2010) Disease-modifying effects of phenobarbital and the NKCC1 inhibitor bumetanide in the pilocarpine model of temporal lobe epilepsy. J Neurosci, 30, 8602-8612.
Cohen, I., Navarro, V., Clemenceau, S., Baulac, M. & Miles, R. (2002) On the origin of interictal activity in human temporal lobe epilepsy in vitro. Science, 298, 1418-1421.
Curia, G., Longo, D., Biagini, G., Jones, R.S. & Avoli, M. (2008) The pilocarpine model of temporal lobe epilepsy. J Neurosci Methods, 172, 143-157.
De Guzman, P., Inaba, Y., Biagini, G., Baldelli, E., Mollinari, C., Merlo, D. & Avoli, M. (2006) Subiculum network excitability is increased in a rodent model of temporal lobe epilepsy. Hippocampus, 16, 843-860.
Delpire, E. (2000) Cation-Chloride Cotransporters in Neuronal Communication. News Physiol Sci, 15, 309-312.
Du, F., Eid, T., Lothman, E.W., Kohler, C. & Schwarcz, R. (1995) Preferential neuronal loss in layer III of the medial entorhinal cortex in rat models of temporal lobe epilepsy. J Neurosci, 15, 6301-6313.
Du, F., Whetsell, W.O., Abou, K.B., Blumenkopf, B., Lothman, E.W. & Schwarcz, R. (1993) Preferential neuronal loss in layer III of the entorhinal cortex in patients with temporal lobe epilepsy. Epilepsy Res, 16, 223-233.

(Continued)

*Primary Examiner* — Sarah Pihonak
(74) *Attorney, Agent, or Firm* — Henry D. Coleman; R. Neil Sudol

(57) ABSTRACT

The invention provides methods of treatment that prevent the onset of Mesial temporal lobe epilepsy (TLE) in a subject, or which reduce the severity of TLE in a subject, by administering a NKCC1 inhibitor to the subject after the subject has suffered from an insult known to precipitate TLE.

11 Claims, 22 Drawing Sheets

(56) References Cited

OTHER PUBLICATIONS

Dube, C., Boyet, S., Marescaux, C. & Nehlig, A. (2000a) Progressive metabolic changes underlying the chronic reorganization of brain circuits during the silent phase of the lithium-pilocarpine model of epilepsy in the immature and adult Rat. Exp Neurol, 162, 146-157.

Dube, C., Marescaux, C. & Nehlig, A. (2000b) A metabolic and neuropathological approach to the understanding of plastic changes that occur in the immature and adult rat brain during lithium-pilocarpine-induced epileptogenesis. Epilepsia, 41 Suppl 6, S36-43.

Egorov, A.V., Angelova, P.R., Heinemann, U. & Müller, W. (2003) Ca2+-independent muscarinic excitation of rat medial entorhinal cortex layer V neurons. Eur J Neurosci, 18, 3343-3351.

Egorov, A.V., Heinemann, U. & Müller, W. (2002) Differential excitability and voltage-dependent Ca2+ signalling in two types of medial entorhinal cortex layer V neurons. Eur J Neurosci, 16, 1305-1312.

El-Hassar, L., Milh, M., Wendling, F., Ferrand, N., Esclapez, M. & Bernard, C. (2007) Cell domain-dependent changes in the glutamatergic and GABAergic drives during epileptogenesis in the rat CA1 region. J Physiol, 578, 193-211.

Fountain, N.B., Bear, J., Bertram,. E.H., 3rd & Lothman, E.W. (1998) Responses of deep entorhinal cortex are epileptiform in an electrogenic rat model of chronic temporal lobe epilepsy. J Neurophysiol, 80, 230-240.

Gorter, J.A., van Vliet, E.A., Aronica, E., Breit, T., Rauwerda, H., Lopes da Silva, F.H. & Wadman, W.J. (2006) Potential new antiepileptogenic targets indicated by microarray analysis in a rat model for temporal lobe epilepsy. J Neurosci, 26, 11083-11110.

Guzowski, J.F., McNaughton, B.L., Barnes, C.A. & Worley, P.F. (1999) Environment-specific expression of the immediate-early gene Arc in hippocampal neuronal ensembles. Nat Neurosci, 2, 1120-1124.

Hamam, B.N., Kennedy, T.E., Alonso, A. & Amaral, D.G. (2000). Morphological and electrophysiological characteristics of layer V neurons of the rat medial entorhinal cortex. J Comp Neurol, 418, 457-472.

Hannaert, P., Alvarez-Guerra, M., Pirot, D., Nazaret, C. & Garay, R.P. (2002) Rat NKCC2/NKCC1 cotransporter selectivity for loop diuretic drugs. Naunyn Schmiedebergs Arch Pharmacol, 365, 193-199.

Huberfeld, G., Wittner, L., Clemenceau, S., Baulac, M., Kaila, K., Miles, R. & Rivera, C. (2007) Perturbed chloride homeostasis and GABAergic signaling in human temporal lobe epilepsy. J Neurosci, 27, 9866-9873.

Kang, T.C., An, S.J., Park, S.K., Hwang, I.K., Yoon, D.K., Shin, H.S. & Won, M.H. (2002) Changes in Na(+)—K(+)—Cl(−) cotransporter immunoreactivity in the gerbil hippocampus following transient ischemia. Neurosci Res, 44, 249-254.

Kobayashi, M., Wen, X. & Buckmaster, P.S. (2003) Reduced inhibition and increased output of layer II neurons in the medial entorhinal cortex in a model of temporal lobe epilepsy. J Neurosci, 23, 8471-8479.

Kumar, S.S. & Buckmaster, P.S. (2006) Hyperexcitability, interneurons, and loss of GABAergic synapses in entorhinal cortex in a model of temporal lobe epilepsy. J Neurosci, 26, 4613-4623.

Li, X., Zhou, J., Chen, Z., Chen, S., Zhu, F. & Zhou, L. (2008) Long-term expressional changes of Na+—K+—Cl-co-transporter 1 (NKCC1) and K+—Cl-co-transporter 2 (KCC2) in CA1 region of hippocampus following lithium-pilocarpine induced status epilepticus (PISE). Brain Res, 1221, 141-146.

Misgeld, U., Deisz, R.A., Dodt, H.U. & Lux, H.D. (1986) The role of chloride transport in postsynaptic inhibition of hippocampal neurons. Science, 232, 1413-1415.

Munoz, A., Mendez, P., DeFelipe, J. & Alvarez-Leefmans, F.J. (2007) Cation-chloride cotransporters and GABA-ergic innervation in the human epileptic hippocampus. Epilepsia, 48, 663-673.

Ormandy, G.C., Jope, R.S. & Snead, O.C., 3rd (1989) Anticonvulsant actions of MK-801 on the lithium-pilocarpine model of status epilepticus in rats. Exp Neurol, 106, 172-180.

Palma, E., Amici, M., Sobrero, F., Spinelli, G., Di Angelantonio, S., Ragozzino, D., Mascia, A., Scoppetta, C., Esposito, V., Miledi, R. & Eusebi, F. (2006) Anomalous levels of Cl-transporters in the hippocampal subiculum from temporal lobe epilepsy patients make GABA excitatory. Proc Natl Acad Sci U S A, 103, 8465-8468.

Pathak, H.R., Weissinger, F., Terunuma, M., Carlson, G.C., Hsu, F.C., Moss, S.J. & Coulter, D.A. (2007) Disrupted dentate granule cell chloride regulation enhances synaptic excitability during development of temporal lobe epilepsy. J Neurosci, 27, 14012-14022.

Payne, J.A., Stevenson, T.J. & Donaldson, L.F. (1996) Molecular characterization of a putative K—Cl cotransporter in rat brain. A neuronal-specific isoform. J Biol Chem, 271, 16245-16252.

Peterson, S.L., Purvis, R.S. & Griffith, J.W. (2005) Comparison of neuroprotective effects induced by alpha-phenyl-N-tert-butyl nitrone (PBN) and N-tert-butyl-alpha-(2 sulfophenyl) nitrone (S-PBN) in lithium-pilocarpine status epilepticus. Neurotoxicology, 26, 969-979.

Russell, J.M. (2000) Sodium-potassium-chloride cotransport. Physiol Rev, 80, 211-276.

Sen, A., Martinian, L., Nikolic, M., Walker, M.C., Thom, M. & Sisodiya, S.M. (2007) Increased NKCC1 expression in refractory human epilepsy. Epilepsy Res, 74, 220-227.

Staley, K.J., Soldo, B.L. & Proctor, W.R. (1995) Ionic mechanisms of neuronal excitation by inhibitory GABAA receptors. Science, 269, 977-981.

Sung, K.W., Kirby, M., McDonald, M.P., Lovinger, D.M. & Delpire, E. (2000) Abnormal GABAA receptor-mediated currents in dorsal root ganglion neurons isolated from Na—K—2Cl cotransporter null mice. J Neurosci, 20, 7531-7538.

Wang, C., Shimizu-Okabe, C., Watanabe, K., Okabe, A., Matsuzaki, H., Ogawa, T., Mori, N., Fukuda, A. & Sato, K. (2002) Developmental changes in KCC1, KCC2, and NKCC1 mRNA expressions in the rat brain. Dev Brain Res, 139, 59-66.

Yamada, J., Okabe, A., Toyoda, H., Kilb, W., Luhmann, H.J. & Fukuda, A. (2004) Cl-uptake promoting depolarizing GABA actions in immature rat neocortical neurones is mediated by NKCC1. J Physiol, 557, 829-841.

Aronica E, Gorter JA. Gene Expression Profiled in Temporal Lobe Epilepsy. The Neuroscientist, 2007;13(2):100-108.

Ballanyi K, Grafe P. An intracellular analysis of gamma-aminobutyric-acid-associated ion movements in rat sympathetic neurones. J Physiol, 1985;365:41-58.

Ben-Ari Y. Excitatory Actions of Gaba During Development: The Nature of the Nurture. Nat Rev Neurosci, 2002;3(9):728-739.

Benardo LS. Prevention of Epilepsy After Head Trauma: Do We Need New Drugs or a New Approach? Epilepsia, 2003;44:27-33.

Brandt C, et al. Treatment with valproate after status epilepticus: Effect on neuronal damage, epileptogenesis, and behavioral alterations in rats. Neuropharmacology, 2006;51:789-804.

Brandt C, et al. Prophylactic treatment with levetiracetam after status epilepticus: Lack of effect on epileptogenesis, neuronal damage, and behavioral alterations in rats. Neuropharmacology, 2007;53:207-221.

Brandt C, et al. Disease-Modifying Effects of Phenobarbital and the NKCC1 Inhibitor Bumetanide in the Pilocarpine Model of Temporal Lobe Epilepsy. The Journal of Neuroscience, 2010;30(25):8602-8612.

Doppenberg EMR, Bullock R. Clinical Neuro-Protection Trials in Severe Traumatic Brain Injury: Lessons from Previous Studies. Journal of Neurotrauma, 1997;14(2):71-80.

Dzhala VI, et al. NKCC1 transporter facilitates seizures in the developing brain. Nature Medicine, 2005;11(11):1205-1213.

Glykys J, et al. Local Impermeant Anions Establish the Neuronal Chloride Concentration. Science, 2014;343:670-675.

Glykys J, Mody I. Hippocampal Network Hyperactivity After Selective Reduction of Tonic Inhibitions in GABA(A) Receptor Alpha5 Subunit-Deficient Mice. J Neurophysiol, 2006;95:2796-2807.

Gorter JA, et al. Potential New Antiepileptogenic Targets Indicated by Microarray Analysis in a Rate Model for Temporal Lobe Epilepsy. The Journal of Neuroscience, 2006;26(43):11083-11110.

(56) References Cited

OTHER PUBLICATIONS

Hannaert P, et al. Rat NKCC2/NKCC1 cotransporter selectivity for loop diuretic drugs. Nauna-Schmiedeberg's Arch Pharmacol, 2002;365:193-199.

Hartmann AM, et al. Differences in the Large Extracellular Loop between the K+—Cl-Cotransporters KCC2 and KCC4. The Journal of Biological Chemistry, 2010;285(31):23994-24002.

Kilb W, Sinning A, Luhmann HJ. Model-specific effects of bumetanide on epileptiform activity in the in-vitro intact hippocampus of the newborn mouse. Neuropharmacology, 2007;53:524-533.

Misgeld U, et al. The Role of Chloride Transport in Postsynaptic Inhibition of Hippocampal Neurons. Science, 1986;232:1413-1415.

Markadieu N, Delpire E. Physiology and Pathophysiology of SLC12A1/2 transporters. Pflugers Arch, 2014;466(1).

Payne JA. Functional characterization of the neuronal-specific K—Cl cotransporter: implications for [K+](0) regulation. The American Physiological Society, 1997:C1516-C1525.

Na+, K+, 2Cl-Cotransport and Intracellular Chloride Regulation in Rat Primary Sensory Neurons: Thermodynamic and Kinetic Aspects. J Neurophysiol, 2008;100:169-184.

Temkin NR. Antiepileptogenesis and Seizure Prevention Trials with Antiepileptic Drugs: Meta-Analysis of Controlled Trials. Epilepsia, 42(4):515-524, 2001.

Tollner K, et al. Bumetanide is not capable of terminating status epilepticus but enhances Phenobarbital efficacy in different rat models. European Journal of Pharmacology, 2015;746:78-88.

Voipio J, et al. Comment on "Local impermeant anion establish the neuronal chloride concentration". Science, 2014;345:1130.

\* cited by examiner

METHODS OF TREATING AND PREVENTING/REDUCING THE LIKELIHOOD OF MESIAL TEMPORAL LOBE EPILEPSY (TLE)

RELATED APPLICATIONS

The present application claims the benefit of priority of International Patent Application No. PCT/US2010/043063, International Filing Date 23 Jul. 2010, entitled "METHODS OF TREATING AND PREVENTING/REDUCING THE LIKELIHOOD OF MESIAL TEMPORAL LOBE EPILEPSY (TLE)", which claims the benefit of priority of provisional application serial number U.S. 61/271,714, filed Jul. 24, 2009 and provisional application serial number U.S. 61/281,095, filed Nov. 12, 2009 all three applications of identical title, and all three of which applications are incorporated by reference in their entirety herein.

FEDERALLY-SPONSORED RESEARCH

The present invention was made with government support under Grant Nos. RR15636, AA015614, AA014127, and AA016880 awarded by NIH/NRSA. Consequently, the government has rights in the invention.

FIELD OF THE INVENTION

The invention provides novel methods of treating and preventing Mesial temporal lobe epilepsy (TLE).

BACKGROUND OF THE INVENTION

Citations for all references are found after the experimental section.

Mesial temporal lobe epilepsy (TLE) is the most common type of epilepsy in adults (Engel, 1989), and frequently becomes resistant to drug therapy, leaving ultimately only a neurosurgery option to control seizures. TLE develops following a variety of insults, including brain injury and status epilepticus (SE). Precipitating insults are followed by a characteristic seizure-free "latent period" lasting typically a few months, in exceptional cases even years, in humans (Annegers et al., 1980; Weiss et al., 1986). The TLE in rats that arises several weeks after a lithium-pilocarpine induced SE reproduces most clinical and neuropathological features of human TLE, and presents a very useful animal model of the disease (Ormandy et al., 1989; Turski et al., 1991; Cavalheiro, 1995; Dube et al., 2000; Andre et al., 2007). Even though initial causes may vary, the behavioral and histo-pathological hallmarks of TLE are remarkably similar in all etiologies. This has led a number of investigators to hypothesize that there is a major common pathway downstream of initiating causes, probably the intense synchronous activity that is a signature of seizures (Du et al., 1995; Wu and Schwarcz, 1998; Schwarcz et al., 2000). This synchronous activity is usually seen in hippocampus and parahippocampal cortices, including the EC (Schwartzkroin and Knowles, 1984; Bartolomei et al., 2004). Over the longer term, specific mesial temporal lobe atrophy has been shown ipsilateral to the seizure focus (Bartolomei et al., 2005). Examination of surgically resected specimens has revealed cell loss and astrogliosis in EC (Yilmazer-Hanke et al., 2000).

Exactly where important early changes in neuronal physiology occur after the SE is unclear; however, neuroprotection experiments of hippocampal Cornu Ammonis (CA) regions vs. parahippocampal cortices suggest a key role of the parahippocampal cortices at the early steps of epileptogenesis (Andre et al., 2007). Moreover, we have observed in previous studies that the deep EC exhibits unusual high network excitation, in striking contrast to layers 2 and 3 (Gloveli et al., 1999; Egorov et al., 2003), suggesting that the deep EC may be particularly susceptible to the development of hyperexcitability triggered by status epilepticus.

An important mechanism in preventing spontaneously recurring seizures (SRS) is Cl-dependent synaptic inhibition of excitatory neurons. The effectiveness of this inhibition decreases with an increase in intracellular Cl-relative to extracellular Cl-concentration. The intracellular Cl-concentration is decreased by K+Cl-co-transporters, particularly KCC2, driven by the K+ outward gradient, and increased by Na+K+2Cl-co-transporters, particularly NKCC1, driven by the Na+ inward gradient. Thus it is well established for peripheral and central neurons that both Cl-transports play an important role for efficiency of synaptic inhibition (Aickin et al., 1984; Misgeld et al., 1986).

U.S. Patent Application Document No. 20070043034 describes the use of diuretic compounds to treat various disorders, in particular sodium potassium chloride cotransport mediated disorders, and disorders associated with excitotoxicity in the brain that are exacerbated by impaired inhibition of gamma aminobutyric acid (GABA).

Notwithstanding efforts to prevent or treat TLE, the need continues to exist for methods of treatment which will prevent or ameliorate the aforementioned TLE-related insults.

SUMMARY OF THE INVENTION

Applicants have discovered methods of treatment that prevent the onset of Mesial temporal lobe epilepsy (TLE) in a subject, or which reduce the severity of TLE in a subject, by administering a NKCC1 inhibitor to the subject after the subject has suffered from an insult known to precipitate TLE.

Thus, in certain aspects of our invention, a NKCC1 inhibitor is administered to the subject after the subject has suffered from insults such as status epilepticus (SE), petit mal epilepsy, absence, myoclonic, clonic, tonic, tonic-clonic, and atonic seizures, acquired aphasia, acquired aphasia with epilepsy (Landau-Kleffner syndrome), acquired epileptic aphasia, cortical dysplasia-focal epilepsy syndrome (CDFE), neonatal seizures, hippocampal sclerosis (HS) and hippocampal, cerebral, and cerebellar atrophy, febrile seizures including complex febrile convulsions (CFC), traumatic brain injury, stroke and after discovery or diagnosis of a brain tumor.

In one aspect, the NKCC1 inhibitor is administered to the subject during the latent period following the subject's development of status epilepticus (SE).

In another aspect, the NKCC1 inhibitor is administered to the subject after the subject suffers an initial seizure of unknown etiology.

In still another aspect, the NKCC1 inhibitor is administered to the subject within around eight to around twenty four weeks (alternatively, about twelve to about sixteen weeks), or within around one to four, or around two or three to four weeks after suffering a TLE precipitating insult (in general, including SE seizures). Times after SE or other TLE precipitating insults for effective treatment of TLE and TLE development by bumetanide and combinations thereof with enhancers of GABAAergic transmission may be much longer, depending on duration or severity of SE or insult, and species, particularly humans.

In other aspects of our invention, the NKCC1 inhibitor and a GABA-modulating composition are co-administered to the subject after the subject has suffered from either an insult known to precipitate TLE or an initial seizure of unknown etiology.

In preferred embodiments of our invention, the NKCC1 inhibitor is a loop diuretic selected from the group consisting of torasemide, furosemide, azosemide, bumetanide, piretanide, tripamide, etozoline and its metabolite ozolinone, and cicletanine, and pharmaceutically acceptable derivatives, salts and esters thereof.

In other aspects of our invention, one or more NKCC1 inhibitors and, optionally, one or more GABA-modulating compositions, are administered chronically to a subject who suffers from recurrent insults known to precipitate TLE.

In another aspect of the invention, the NKCC1 inhibitor(s) is combined with a second therapeutic agent and co-administered to the subject after the subject has suffered from an insult known to precipitate TLE, wherein the second therapeutic agent comprises a GABA modulating composition (e.g., a modulator of gamma-aminobutyric acid A (GABA$_A$) receptor dependent signal transduction), an anticonvulsant agent, an ion channel inactivator, an antidiuretic agent, or a combination thereof.

The inventors have discovered that during the period that follows an insult known to precipitate TLE (e.g. during the latent period after SE), an increasing percentage of neurons in EC layer 5 respond to a single synaptic stimulus with polysynaptic burst depolarizations/epileptiform activity. This change is paralleled by a progressive depolarizing shift of the IPSP reversal potential in layer 5 neurons, apparently caused by upregulation of the Cl$^-$ inward transporter NKCC1 and concurrent downregulation of the Cl$^-$ outward transporter KCC2, both changes favoring intracellular Cl$^-$ accumulation. Inhibiting Cl-uptake in the latent period restored more negative GABAergic reversal potentials and eliminated polysynaptic bursts. The changes in the Cl$^-$ transporters were highly specific to the deep entorhinal cortex. They did not occur in layers 1-3, perirhinal cortex, subiculum, CA1, CA3, or dentate gyrus during this period. While not wishing to be bound by any theory, we propose that the changes in Cl$^-$ homeostasis facilitate hyperexcitability in the deep entorhinal cortex leading to epileptiform discharge there, which subsequently affects downstream cortical regions.

Methods of treatment of the invention thus target a specific fundamental pathology underlying abnormal cellular activity and seizure generation during the latent period and following early chronic epilepsy. Chronic inhibition of NKCC1 after an insult known to precipitate TLE or after an initial seizure of unknown etiology, proves useful in prophylactic prevention, or attenuation of development of TLE.

These and other aspects of the invention are described further in the Detailed Description of the Invention.

DETAILED DESCRIPTION OF THE INVENTION

Figure 1:
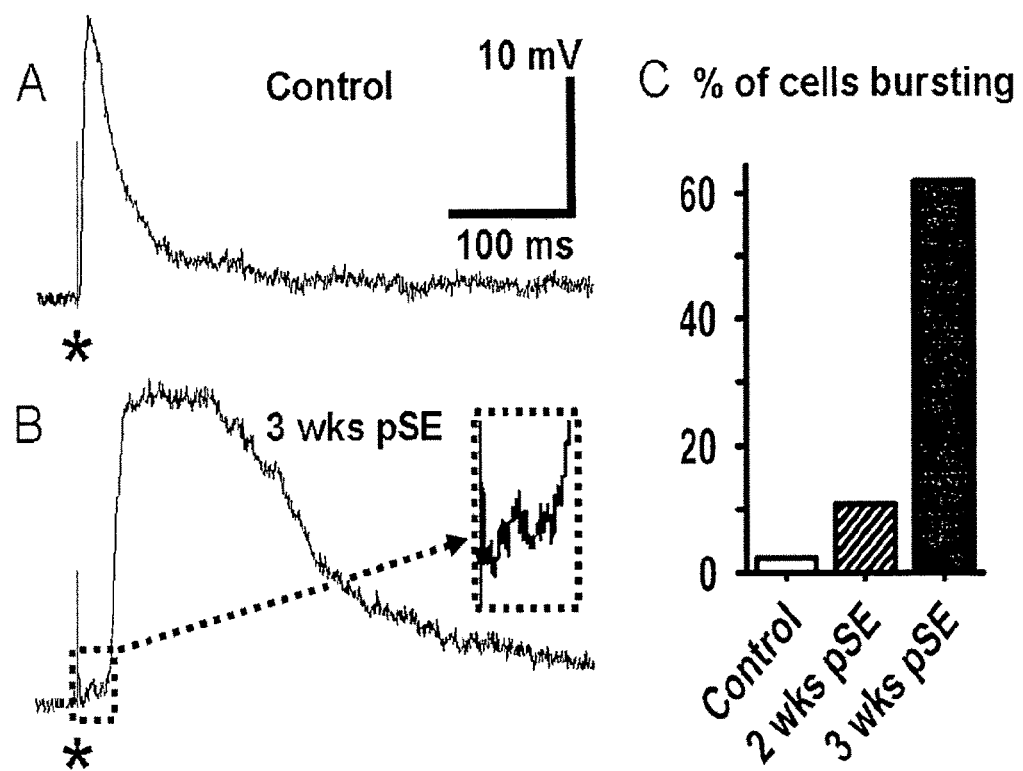
FIG. 1 illustrates increased polysynaptic burst excitation in EC L5 neurons post SE, as determined in the experiment(s) of Example 1.

The following terms shall be used to describe the present invention. In cases where a term is not specifically defined herein, the term shall be given a common meaning used by those of ordinary skill in the art consistent with the use of that term within the context of describing the present invention.

Unless otherwise specified, "a," "an," "the," and "at least one" are used interchangeably and mean one or more than one.

The term "effective" is used to describe an amount of a component of the present invention which is used for producing an intended effect in the present invention.

"GABA-modulating compositions" include, but are not limited to, barbiturates (e.g. phenobarbital), benzodiazepines (e.g. diazepam), or drugs that increase GABA-release or inhibit GABA re-uptake, e.g. Gabapentin, Pregabalin, 4-aminobutanoic acid (GABA), 4-amino-3-(4-chlorophenyl)butanoic acid (baclofen), 4-amino-3-phenylbutanoic acid, 4-amino-3-hydroxybutanoic acid, 4-amino-3-(4-chlorophenyl)-3-hydroxyphenylbutanoic acid, 4-amino-3-(thien-2-yl)butanoic acid, 4-amino-3-(5-chlorothien-2-yl)butanoic acid, 4-amino-3-(5-bromothien-2-yl)butanoic acid, 4-amino-3-(5-methylthien-2-yl)butanoic acid, 4-amino-3-(2-imidazolyl)butanoic acid, 4-guanidino-3-(4-chlorophenyl)butanoic acid, (3-aminopropyl)phosphonous acid, (4-aminobut-2-yl)phosphonous acid, sodium butyrate, (3-amino-2-methylpropyl)phosphonous acid, (3-aminobutyl)phosphonous acid, (3-amino-2-(4-chlorophenyl)propyl) phosphonous acid, (3-amino-2-(4-chlorophenyl)-2-hydroxypropyl)phosphonous acid, (3-amino-2-(4-fluorophenyl)propyl)phosphonous acid, (3-amino-2-phenylpropyl)phosphonous acid, (3-amino-2-hydroxypropyl)phosphonous acid, (E)-(3-aminopropen-1-yl)phosphonous acid, (3-amino-2-cyclohexylpropyl) phosphonous acid, (3-amino-2-benzylpropyl)phosphonous acid, [3-amino-2-(4-methylphenyl)propyl]phosphonous acid, [3-amino-2-(4-trifluoromethylphenyl)propyl]phosphonous acid, [3-amino-2-(4-methoxyphenyl)propyl]phosphonous acid, [3-amino-2-(4-chlorophenyl)-2-hydroxypropyl] phosphonous acid, (3-aminopropyl)methylphosphinic acid, (3-amino-2-hydroxypropyl)methylphosphinic acid, (3-aminopropyl)(difluoromethyl)phosphinic acid, (4-aminobut-2-yl)methylphosphinic acid, (3-amino-1-hydroxypropyl)methylphosphinic acid, (3-amino-2-hydroxypropyl)(difluoromethyl)phosphinic acid, (E)-(3-aminopropen-1-yl) methylphosphinic acid, (3-amino-2-oxo-propyl) methylphosphinic acid, (3-aminopropyl) hydroxymethylphosphinic acid, (5-aminopent-3-yl) methylphosphinic acid, (4-amino-1,1,1-trifluorobut-2-yl) methylphosphinic acid, (3-amino-2-(4-chlorophenyl) propyl)sulfinic acid, and 3-aminopropylsulfinic acid.

Other compositions which may be of use as gaba-modulating compositions in the present invention include:

Agonists: including Gaboxadol • Isoguvacine • Isonipecotic Acid • Muscimol (Amanita Muscaria) • Progabide • SL 75102 • Thiomuscimol;

$GABA_A$ Receptor Positive Allosteric Modulators including:

Barbiturates

Allobarbital • Alphenal • Amobarbital • Aprobarbital • Barbexaclone • Barbital • Benzylbutylbarbiturate • Brallobarbital • Brophebarbital • Bucolome • Butabarbital • Butalbital • Butobarbital • Butallylonal • Crotylbarbital • Cyclobarbital • Cyclopal • Enallylpropymal • Ethallobarbital • Febarbamate • Heptabarbital • Hexethal • Hexobarbital • Mephobarbital • Metharbital • Methohexital • Methylphenobarbital • Narcobarbital • Nealbarbital • Pentobarbital • Phenobarbital • Phetharbital • Primidone • Prazitone • Probarbital • Propallylonal • Proxibarbal • Proxibarbital • Reposal • Secbutabarbital • Secobarbital • Sigmodal • Spirobarbital • Talbutal • Thialbarbital • Thiamylal • Thiobarbital • Thiobutabarbital • Thiopental • Valofane • Vinbarbital • Vinylbital Benzodiazepines Adinazolam • Alprazolam • Arfendazam • Avizafone • Bentazepam • Bretazenil • Bromazepam • Brotizolam • Camazepam • Chlordiazepoxide • Ciclotizolam • Cinolazepam • Climazolam • Clobazam • Clonazepam • Clorazepate • Clotiazepam • Cloxazolam • Cyprazepam • Delorazepam • Diazepam • Doxefazepam • Elfazepam • Estazolam • Ethyl Carfluzepate • Ethyl Dirazepate • Ethyl Loflazepate • Etizolam • Fletazepam • Fludiazepam • Flunitrazepam • Flurazepam • Flutazolam • Flutemazepam • Flutoprazepam • Fosazepam • Gidazepam • Girisopam • Halazepam • Haloxazolam • Iclazepam • Imidazenil • Ketazolam • Lofendazam • Lopirazepam • Lopirazepam • Loprazolam • Lorazepam • Loiinetazepam • Meclonazepam • Medazepam • Menitrazepam • Metaclazepam • Mexazolam • Midazolam • Nerisopam • Nimetazepam • Nitrazepam • Nitrazepate • Nordazepam • Oxazepam • Oxazolam • Phenazepam • Pinazepam • Pivoxazepam • Prazepam • Premazepam • Proflazepam • QH-II-66 • Quazepam • Reclazepam • Rilmazafone • Ripazepam • Ro48-6791 • SH-053-R-CH3-2'F • Sulazepam • Temazepam • Tetrazepam • Tofisopam • Triazolam • Triflubazam • Uldazepam • Zapizolam • Zolazepam • Zomebazam Carbamates Carisbamate • Carisoprodol • Emylcamate • Felbamate • Mebutamate • Meprobamate • Methocarbamol • Phenprobamate • Procymate • Tybamate Neuroactive Steroids Acebrochol • Allopregnanolone • Alphadolone • Alphaxolone • Ganaxolone • Hydroxydione • Minaxolone • Org 20599 • THDOC Nonbenzodiazepines Abecarnil • Adipiplon • Alpidem • CGS-20625 • CGS-9896 • CL-218,872 • ELB-139 • Eszopiclone • Etifoxine • Gedocarnil • Indiplon • L-838,417 • Necopidem • NS-2664 • NS-2710 • Ocinaplon • Pagoclone • Panadiplon • Pazinaclone • Pipequaline • ROD-188 • RWJ-51204 • Saripidem • SB-205,384 • SL-651,498 • Suproclone • Suriclone • SX-3228 • TP-003 • TPA-023 • TP-13 • Tracazolate • U-89843A • U-90042 • Y-23684 • Zaleplon • Zolpidem • Zopiclone Phenols Fospropofol • Propofol • Thymol Piperidinediones Glutethimide • Methyprylon • Piperidione • Pyrithyldione Quinazolinones Afloqualone • Cloroqualone • Diproqualone • Etaqualone • Mebroqualone • Mecloqualone • Methaqualone • Methylmethaqualone Others
Chlormezanone • Clomethiazole • Etazolate • Ethanol (Alcohol) • Etomidate • Kavalactones (Kava Kava) • Loreclezole • Progabide • Propanidid • ROD-188 • Skullcap • Stiripentol • Valerenic Acid (Valerian)

Inhibitors of Na(+)-K(+)-2Cl(−) cotransporters (bumetanide or ethacrynic acid *Am J Physiol Renal Physiol.* 2009 February; 296(2):F446-57.

The serine-threonine kinase WNK4 proved to be a potent inhibitor of the activity of both the Na(+)-K(+)-2Cl(−) cotransporter (NKCC1) and the Cl(−)/base exchanger SLC26A6 (CFEX) (Proc Natl Acad Sci USA. 2004 Feb. 17; 101(7):2064-9. Epub 2004 Feb. 9)

Expression of NKCC1 protein from mRNA may be inhibited with antisense strands of nucleic acids targeted to the entorhinal cortex during the re-expression period.

Inflammation typically leads to up-regulation of NKCCs, particularly NKCC1. Typical signs of inflammation have been demonstrated in epileptogenic cortex, and inflammatory mediators may therefore contribute to NKCC1 re-expression. Thus, prolonged interferon-gamma exposure can decreases ion transport and NKCC1 expression in other tissues (Am J Physiol Gastrointest Liver Physiol. 2004 January; 286(1):G157-65. Epub 2003 Sep. 4), and may thus be useful for inhibiting the shown NKCC1 re-expression in EC after a TLE precipitating insult.

GABAB receptor blockers would be useful to increase GABA release by blocking negative feedback on release by activation of GABAB receptors Antagonists: Main Site: Phaclofen • Saclofen • SCH-50911.

Blockage of GABA catabolism may also be useful: GABA-T Inhibitors, such as 3-Hydrazinopropionic Acid • Aminooxyacetic Acid • Gabaculine • Gabapentin • Isoniazid • Phenelzine • Phenylethylidenehydrazine • Pregabalin • Valnoctamide • Valproic acid • Valpromide • Vigabatrin.

Inhibition of diuretic effects of NKCC1 inhibitors may be useful to minimize side effects on water and sodium homeostasis. 1) Pretreatment with probenecid can reduce both the natriuresis and hyperreninemia produced by bumetanide or other NKCC1 inhibitors. These antagonistic effects of probenecid on NKCC inhibition-mediated natriuresis is apparently not due to a direct action on sodium excretion but is probably secondary to its inhibitory effect on renal tubular secretion of bumetanide. 2) Indomethacin blunts the increases in urine volume and sodium excretion seen during bumetanide treatment and inhibits the bumetanide-induced increase in plasma renin activity. 3) Arginine vasopressin (AVP), also known as vasopressin, argipressin or antidiuretic hormone (ADH), and variants, e.g. lysine vasopressin (LVP) or lypressin, blunt the increase in water diuresis caused by inhibition of NKCC in the kidney by increasing water re-absorption in the distal tubule and collecting duct in the kidney.

Anticonvulsant agents are a diverse group of pharmaceuticals, including ion channel inactivators, used in the treatment of epileptic seizures in order to inhibit build-up and spread of neuronal seizure activity. They may be useful to further suppress epileptiform activity and downstream changes increasing excitability. This is particularly important when epileptiform activity becomes less dependent on NKCC1 activity during progression of the disease in the chronic period. Carbamazepine and phenytoin are both present first choice anticonvulsants. Both drugs stabilize the inactivated state of sodium channels, making neurons less likely to fire action potentials, and may have also other effects.

Gabapentin's exact mechanism of action is unknown, but its anticonvulsant action is thought to involve voltage-gated N-type calcium ion channels. Valproic acid/valproate also block the voltage-gated sodium channels and T-type Calcium channels. These mechanisms make valproic acid/valproate a broad spectrum anticonvulsant drug. Other clinically used anticonvulsants are levetiracetam lamotrigine, primidone, and felbamate and are particularly of benefit when carbamazepine and phenytoin fail. Other anticonvulsants that may be useful are bromides (potassium bromide), carbamates (felbamate), carboxamides (carbamazepine, oxcarbazepine, eslicarbazepine acetate, fatty acids (valproates—valproic acid, sodium valproate, and divalproex sodium, vigabatrin, progabide, tiagabine, fructose derivatives (topiramate), GABA analogs (gabapentin, pregabalin, hydantoins (Ethotoin, phenytoin, mephenytoin, fosphenytoin), oxazolidinediones (paramethadione, trimethadione, ethadione), propionates (beclamide), pyrimidinediones (primidone), pyrrolidines (brivaracetam, levetriacetam, seletracetam), succinimides (ethosuximide, phensuximide, mesuximide), sulfonamides (acetazolamide, sultiame, methazolamide, zonisamide), triazines (lamotrigine), ureas (pheneturide, phenacemide), valproylamides (amide derivatives of valproate), amides (valpromide, valnoctamide).

"An insult known to precipitate TLE" includes, but is not limited to, status epilepticus (SE), petit mal epilepsy, absence, myoclonic, clonic, tonic, tonic-clonic, and atonic seizures, acquired aphasia, acquired aphasia with epilepsy (Landau-Kleffner syndrome), acquired epileptic aphasia, cortical dysplasia-focal epilepsy syndrome (CDFE), neonatal seizures, hippocampal sclerosis (HS) and hippocampal, cerebral, and cerebellar atrophy, febrile seizures including complex febrile convulsions (CFC), and traumatic brain injury, strokes, brain tumors, infections, spinal meningitis, encephalitis, blood vessel malformations.

"NKCC1 inhibitors" include, but are not limited to, loop diuretics (i.e. diuretics which inhibit the $Na^+/K^+/2Cl^-$ carrier in the thick ascending limb of the loop of Henle and thereby inhibit the reabsorption of sodium, potassium and chloride ions. Useful loop diuretics are torasemide, furosemide, azosemide, bumetanide, piretanide, tripamide, etozoline and its metabolite ozolinone, and cicletanine, and pharmaceutically acceptable derivatives thereof, for example salts and esters thereof). Other NKCC1 inhibitors include GABA-T Inhibitors: 3-Hydrazinopropionic Acid, Aminooxyacetic Acid, Gabaculine, Gabapentin, Isoniazid, Phenelzine, Phenylethylidenehydrazine, Pregabalin, Valnoctamide, Valproic acid, Valpromide, Vigabatrin, among others.

The term "patient" or "subject" is used throughout the specification within context to describe an animal, generally a mammal and preferably a human, to whom treatment, including prophylactic treatment, with the compositions according to the present invention is provided. For treatment of those infections, conditions or disease states which are specific for a specific animal such as a human patient, the term patient refers to that specific animal.

As used herein, the term "treating" refers to preventing, slowing, delaying, stopping or reversing the progression of a condition.

As used herein, the term "therapeutically effective amount" refers to the amount of a NKCC1 inhibitor (optionally in combination with one or more GABA-modulating compositions) that is in sufficient quantities to treat a subject having, or at risk of developing, TLE. For example, an effective amount is sufficient to delay, slow, or prevent the onset or progression of TLE or related symptoms.

The term "inhibitory effective concentration" or "inhibitory effective amount" is used throughout the specification to describe concentrations or amounts of compounds according to the present invention which substantially or significantly treat or prevent TLE or related symptoms.

The term "preventing effective amount" is used throughout the specification to describe concentrations or amounts of compounds according to the present invention which are prophylactically effective in preventing, reducing the likelihood of the onset of TLE or related symptoms. The terms inhibitory effective amount or preventive effective amount also generally fall under the rubric "effective amount".

"Reduce the severity of TLE in a subject" means inhibiting or ameliorating to any beneficial extent any of the numerous symptoms associated with TLE. Solely by way of example, methods of treatment of the invention may ameliorate or lessen the harmful effects of simple partial seizures (SPS) which involve small areas of the temporal lobe and which do not affect consciousness. These are seizures which primarily cause sensations. These sensations may be mnestic such as déjà vu (a feeling of familiarity), jamais vu (a feeling of unfamiliarity), a specific single or set of memories, or amnesia. The sensations may be auditory such as a sound or tune, or gustatory such as a taste, or olfactory such as a smell that is not truly present. Sensations can also be visual or involve feelings on the skin or in the internal organs. The latter feelings may seem to move over the body. Dysphoric or euphoric feelings, fear, anger, and other sensations can also occur during SPS. Often, it is hard for persons with SPS of TLE to describe the feeling. SPS are often called "auras," and are sometimes thought to be preludes to more severe seizures. Such sensations are lessened by application of methods of the invention. In other examples, the severity of complex partial seizures (CPS) is lessened by application of methods of the invention. Such seizures impair consciousness to some extent, usually begin with an SPS, and then spread to a large portion of the temporal lobe. Signs may include motionless staring, automatic movements of the hands or mouth, inability to respond to others, unusual speech, or unusual behaviors. In still another example, methods of the invention reduce the severity of symptoms associated with Secondarily Generalized Tonic-Clonic Seizures (SGTCS). These begin with an SPS or CPS phase initially, but then the arms, trunk and legs stiffen in either a flexed or extended position. After this, coarse jerking of the limbs and trunk occur.

The term "co-administration" is used to describe the administration of two or more active compounds in amounts that are effective to treat or prevent the onset of TLE or related symptoms. Although the term co-administration preferably includes the administration of two active compounds to the patient at the same time, it is not necessary that the compounds actually be administered at the exact same time, only that amounts of compound will be administered to a patient or subject such that effective concentrations are found in the blood, serum or plasma, or in the pulmonary tissue at the same time.

"Administered chronically" or "chronic administration" mean administering a NKCC1 inhibitor and, optionally, a GABA-modulating composition more than once over a period of time that may vary depending upon the condition of the subject and the symptoms presented by the subject during the course of treatment.

Methods of the invention may use dosage forms in which a NKCC1 inhibitor and a GABA-modulating composition are combined with a carrier material. Dosage forms and routes of administration will vary depending upon the subject treated and the state of TLE or related symptoms. In same aspects, methods of the invention entail administration of dosage forms containing between about 0.25 milligram to about 1 gram, more preferably about 1 milligram to about 750 milligrams, and even more preferably about 10 milligrams to about 500-600 milligrams of NKCC1 inhibitor and a GABA-modulating composition.

It should also be understood that a specific dosage and treatment regimen for any particular subject will depend upon a variety of factors, including the activity of the specific compound employed, the age, body weight, general health, sex, diet, time of administration, rate of excretion, drug combination, and the judgment of the treating physician and the severity of the particular disease or condition being treated.

Administration of the active compound may range from continuous (intravenous drip) to several oral administrations per day (for example, Q.I.D.) and may include oral, topical, parenteral, intramuscular, intravenous, sub-cutaneous, transdermal (which may include a penetration enhancement agent), buccal and suppository administration, among other routes of administration. Enteric coated oral tablets may also be used to enhance bioavailability of the compounds from an oral route of administration. The most effective dosage form will depend upon the pharmacokinetics of the particular agent chosen as well as the severity of disease in the patient. Oral dosage forms are particularly preferred, because of ease of administration and prospective favorable patient compliance.

The invention is described further in the following experimental section, which is illustrative only and is not limiting.

Experimental Section

Materials and Methods

TLE induction.

All procedures were approved by the Institutional Animal Care and Use Committee at the University of New Mexico Health Sciences Center and were in accordance with National Institutes of Health Guide for the Care and Use of Laboratory Animals. Our protocol for the experiments here was a slight modification of a protocol published by Andre et al. (Andre et al., 2007). Twenty four hours prior to seizure induction, male Wistar rats, 2-3 months old, were administered s.c. 3 mmol/kg lithium chloride dissolved in isotonic NaCl saline Pilocarpine was then administered s.c. (25 mg/kg in isotonic NaCl). Once generalized limbic convulsions began, subcutaneous needle EEG electrodes were placed to confirm the development of status epilepticus (SE), defined as the occurrence of continuous high amplitude EEG spiking (Ormandy et al., 1989). These needles were fashioned from 25 gauge hypodermic needles (Becton Dickinson), with the hub cut off and bent at 60 degree angles so they will stay in place. One needle was inserted subcutaneously in the scalp over the parietal cortex and the other, which served as the reference electrode, over the scapula. The EEG recordings, using a Grass Model 8 electroencephalograph (Astro-Med, West Warwick, R.I.), showed continuous high amplitude spiking for a 1 hour period following the onset of SE, in clear contrast to normal EEGs, recorded in a previous study with intracranial implanted electrodes (Peterson et al., 2005). Recording was then generally discontinued. Atropine sulfate (10 mg/kg s.c.) and Diazepam (4 mg/kg i.m.) were administered in order to improve survival, decrease anxiety and induce muscle relaxation. This dose of Diazepam did not stop seizures but induced muscle relaxation within one hour and rats were lying on their ventral side, not using their limbs. Nor did atropine stop seizures. 12 hours after SE onset the EEG was recorded again for 5-10 min, and all rats had intermittent or organized, i.e. bursts of EEG spiking. Those rats that showed organized EEG spiking at this time, such as bursts of spiking or continuous trains of spiking (~20% of cases) received an additional 2 mg/kg diazepam, i.m. 5% dextrose in Ringers solution was administered s.c. 12 hours following SE onset.

This protocol differs from the one of Andre et al. (Andre et al., 2007) in that we administered diazepam 1 hour after onset of SE instead of 2 hours. In addition, we applied atropine to reduce peripheral pilocarpine effects (Du et al., 1995). We therefore believe that our protocol should provide a milder insult to the animals.

The protocol of Andre et al. was shown to reliably induce epilepsy in 100% of adult rats (Dube et al., 2000b; Andre et al., 2007). This is also true of an earlier protocol from the same lab that used a slightly higher pilocarpine dose with lithium (Dube et al., 2000b; Andre et al., 2007). In our lab a previous study using the Andre protocol (Andre et al., 2007) showed all rats developing spontaneous rank 3, 4 or 5 seizures after a latent period of 28.6±2.43 (SEM) days (n=14; continuous 24 hour/day video recording, S. Peterson, unpublished results). Only 1 rat had a seizure by day 15. By day 21 4 rats had experienced a seizure, From fitting these latency data with a normal distribution it is expected that on average ~25% of rats have had a first seizure within 3 weeks of the pilocarpine/2 hr Diazepam treatment. However, we never observed seizures during observing and handling rats prior to sacrifice. The epileptic outcome for our mild protocol was tested 8-16 weeks post SE with video recordings of up to a total of 36 hours/rat, and, indeed, over this period spontaneous seizures were observed in all 13 rats. With two new groups of SE rats (total of 12 rats) we determined a latent period duration of 12.7±1.7 weeks (mean±s.e.m.). A total of 203 rats was used, 56 Li-control rats, 42 rats 2 weeks post SE, 47 rats 3 weeks post SE, and 58 rats post SE for video recording.

Slice Preparation.

All experiments were performed on acute horizontal brain slices containing temporal neocortex, entorhinal cortex, subiculum and the ventral hippocampus. Control, or rats 2 or 3 weeks post-seizure, were anesthetized deeply with a mixture of ketamine and xylazine (85 and 15 mg/ml, respectively) and decapitated. The brains were removed rapidly and placed in an oxygenated (95% $O_2$/5% $CO_2$) ice-cold cutting solution containing (in mM): 3 KCl, 1.25 $NaH_2PO_4$, 6 $MgSO_4$, 26 $NaHCO_3$, 0.2 $CaCl_2$, 10 glucose, 220 sucrose, and 0.43 ketamine. Slices (350 μm) were cut in ice-cold cutting solution with a vibratome (Dosaka DTK-1000) and transferred from there into Artificial Cerebro-Spinal Fluid (ACSF, in mM: 126 NaCl, 3 KCl, 1.25 $NaH_2PO_4$, 1 $MgSO_4$, 26 $NaHCO_3$, 2 $CaCl_2$, and 10 glucose) equilibrated with 95% $O_2$/5% $CO_2$ at 34° C. temperature for recovery. After 1 hr ACSF was changed again, and the slices were held at room temperature until used for recording.

Electrophysiology.

Individual slices were transferred to a recording chamber mounted on a fixed-stage microscope (Zeiss Axioskop, Jena, Germany) and superfused with warmed (34° C.), oxygenated ACSF at 2 ml/min. Intracellular recordings were made from EC layer 5 neurons with borosilicate glass sharp microelectrodes (80-150 MΩ) filled with either 1 M $K_2SO_4$, or 0.5 M potassium acetate/0.5 M KCl for lower electrode resistance, or 2 M $CsSO_4$/0.1 M KCl for improved space clamp. In the absence of Cl⁻ transport blockers all intracellular solutions gave identical results for the $GABA_A$ergic PSP reversal potential that were therefore pooled (see also: (Misgeld et al., 1986)). During Cl⁻ transport block by bumetanide it was found that sharp microelectrodes filled with 0.5 M potassium acetate/0.5 M KCl-filled sharp microelectrode did shift EIPSP in depolarizing direction by ~20 mV. Therefore all final recordings/data for bumetanide effects on GABAergic PSP reversal potential were obtained with microelectrodes filled with 1 M $K_2SO_4$ or 2 M $CsSO_4$/ 0.1 M KCl.

Neurons were impaled in the medial entorhinal cortex just above the angular bundle, up to ¼ of cortex thickness, using a Nanostepper micropositioner (Scientific Precision Instruments, Oppenheim, Germany). Recordings were made using an Axoclamp 2B amplifier and digitized and recorded using an Axon Instruments Digidata 1322A (Molecular Devices, Union City, Calif.). Neurons with a RMP negative to −68 mV were tested with hyperpolarizing pulses to ~−85 mV for the presence of Ih indicative of pyramidal neurons (Egorov et al., 2002; Egorov et al., 2003). By this criterion 75% of the recorded population was pyramidal with the remainder presumably multipolar neurons. In a study by Hamam et al. even 85% of neurons impaled with a sharp electrode in L5 showed a prominent long apical dendrite typical for pyramidal neurons (Hamam et al., 2000). In contrast to our studies this study reported presence of Ih also in non-pyramidal neurons (Hamam et al., 2000). Concentric bipolar stimulating electrodes (200 μm diameter, FHC Inc., ME, USA) were placed in layer 5 of EC, ~150-250 μm from the recording electrode. Stimuli (70-100 μs, 100-800 nA) were controlled by a Master 8 programmable pulse generator connected to a stimulus isolation unit (A.M.P.I., Jerusalem, Israel). Full input-output relations for the EPSP and the IPSP were recorded, and stimulation intensities giving 70-90% of maximal response were used. Where indicated stimulation intensity was reduced to elicit 5-10% of maximal response.

FIG. 2A shows the protocol used to determine the reversal potential for $GABA_A$ receptor-mediated, postsynaptic potentials. Monosynaptic PSPs were elicited in the presence of glutamate receptor blockers CNQX (10 μM) and APV (50 μM). Stimulation intensity was adjusted to give approximately 80% of maximal evoked PSP amplitude. Prior to the field stimulus, the membrane voltage (Vm) was changed by either a negative or a positive DC current pulse (500 ms, ≤400 pA). After Vm reached steady state, the PSP was evoked (*). I-V relationships of both the steady membrane potential (FIG. 2B, o's) and peak voltage of the PSP (FIG. 2B, x's), were plotted and the linear regressions calculated using SigmaPlot, giving directly the membrane conductance values. By measuring the I-Vs in the potential range of linear membrane behavior (−80 to −50 mV) we avoided errors in the slope conductance due to voltage-dependent activation of delayed rectifier or other rectifying currents. Reversal potential was determined by the intersection point of the regression lines. Typical PSP traces are shown for both a control and a test animal at 3 weeks. CNQX, DL-2-Amino-5-phosphonopentanoic acid, picrotoxin, bumetanide, pilocarpine, and atropine were obtained from Sigma, St. Luis, Mo. Diazepam was from Hospira Inc., Lake Forest, Ill. Stock solutions, 1000-fold concentrated, were stored in the freezer, and were diluted prior to use in ACSF. For stock solutions, CNQX and picrotoxin were dissolved in DMSO, bumetanide in ethanol. Neither DMSO (1:1000) nor ethanol (1:1000) had any effect on PSPs, I-V relations, or burst responses.

Immunoblotting.

For immunoblotting studies, layer 5-6 of medial EC (=tissue adjacent to the angular bundle and up to ~25% of cortical thickness; the angular bundle is well visible in trans-illumination) were dissected from the 350 μm thick slices, snap-frozen on dry ice and stored at −80° C. till processed. For preparation of membrane fractions the tissues were homogenized in buffer containing 250 mM sucrose, 10 mM Tris-HCl, 10 mM HEPES, 1 mM EDTA and protease inhibitors (pH 7.2) followed by differential centrifugation as described previously (Payne et al., 1996). The purified membrane fraction (50 μg) was then processed for SDS-polyacrylamide gel electrophoresis (7%) and immunoblotting with anti-KCC2 (1:1000; NeuroMab clone N1/12, UC Davis) and anti-actin (1:500; Sigma) antibodies respectively. Antigen-antibody complex was detected by enhanced chemiluminescence (ECL-plus from Amersham, Arlington Heights, Ill.) and x-ray films were quantified using NIH ImageJ software.

Fluorescence In-Situ Hybridization (FISH).

When preparing brain slices for FISH, one brain hemisphere was quick-frozen in a beaker of isopentane equilibrated in dry ice/ethanol slurry and stored at −80° C. Horizontal brain sections (16 μm) were prepared using a cryostat and arranged on slides (Superfrost Plus, VWR), air dried and stored frozen at −80° C. until processed.

NKCC1 (clone ID 4824556, accession number BC033003) and KCC2 (clone ID 6838880, accession number BC054808) plasmids were obtained from Open Biosystems (Huntsville, Ala.). The NKCC1 cDNA sequence was inserted into a pBluescriptR vector between the SalI/XhoI and BamHI restriction sites. KCC2 cDNA sequence was inserted into a pYX-Asc vector between the EcoRI and NotI sites. The plasmids were then sequenced to confirm the NKCC1 and KCC2 sequences (DNA Research Services, University of N. Mex., Health Sciences Center). EcoR1 and Not1 were both used to generate the antisense strand of different lengths, and Kpn1 for the sense strand (New England Biolabs Inc., Ipswich, Mass.). The antisense strand for KCC2 was generated using AscI, and PacI for the sense strand. The restriction digestion reaction was incubated for 2 hours at 37° C.

Single-labeled FISH for NKCC1a,b and KCC2a,b was performed as previously described (Guzowski et al., 1999). Briefly, digoxigenin-labeled KCC2 and NKCC1 whole length antisense riboprobes were generated from linearized cDNA using a commercially available transcription kit (Maxiscript; Ambion, Austin, Tex.) and premixed RNA digoxigenin labeled nucleotides using T3 polymerase (Roche Molecular Biochemicals, Palo Alto, Calif.). Hybridization of both NKCC1 and KCC2 digoxigenin-labeled riboprobes was done overnight at 56° C. on separate slides (1 ng/μl). Then, anti-digoxigenin horseradish peroxidase conjugate (HRP; 1:200; Roche Molecular Biochemicals, Palo Alto, Calif.) was incubated overnight at 4° C. TSA-cyanine-3 (Cy3) (1:50; PerkinElmer, Waltham, Mass.) was used to detect the HRP conjugate. Nuclei were counterstained with 4′, 6′-diamidino-2-phenylindole (DAPI) (1:500; Invitrogen, Carlsbad, Calif.). Images were acquired with Nikon TE2000U epifluorescence microscope (20× objective) equipped with a spinning disk confocal system (Spinning Disk Confocal Imager CARV, Atto Bioscience, Rockville, Md.) and CoolSNAP-Hq CCD Camera (Roper Scientific, Tucson, Ariz.). The images were further analyzed using MetaMorph software (Universal Imaging) and quantified using NIH ImageJ software. Signals were corrected for background (obtained with ROIs covering clearly negative areas in the image), and ratios against nuclear stains were calculated. Where indicated these data were normalized relative to data for control rats.

Immunohistochemistry.

Slices were fixed overnight with 4% paraformaldehyde in 100 mM phosphate buffered saline (PBS), cryoprotected in 15% and 30% sucrose in PBS and then frozen in Optimal Cutting Temperature (OCT) compound (Sakura Finetek, Torrance, Calif.). Immunohistochemistry was performed at room temperature for 24 hours on 300 μm floating sections with anti-KCC2 (NeuroMab clone N1/12, UC Davis) or NKCC1 antibodies (rabbit polyclonal, Chemicon, Temecula, Calif.; results were in agreement with results obtained with mouse NKCC monoclonal antibody MAb T4, kindly provided by Dr. C. Lytle, UC Riverside). Slices were mounted on glass slides and images were taken with a Biorad two-photon microscope and 40× objective 75 μm below the slice surface. NeuroTrace fluorescent Stain (Molecular Probes, Eugene, Oreg.) was used for counterstaining neurons in 60 μm sections prepared from slices using a cryostat, and images were taken with an epifluorescence microscope with CCD camera and a 40× objective. For immuno-staining with NKCC1 antibody tissue sections were pretreated in 1% SDS and 8% 2-mercaptoethanol for 5 minutes before blocking (Sung et al., 2000). In many attempts without this pretreatment we failed to obtain clear NKCC signals with the MAb T4 antibody. All sections were blocked with 10% normal goat serum in PBS-T (PBS containing 0.2% Triton-X-100) and incubated at 4° C. overnight with the respective primary antibodies (1:200). After extensive washes in PBS-T, tissue sections were incubated in Cy3-conjugated goat anti-mouse or anti-rabbit IgG (1:200, Jackson Immuno Research, West Grove, Pa.). Controls received identical treatment without primary antibody and were always negative. Sections were extensively rinsed in PBS-T and cover-slipped for viewing. Hoechst 33342 DNA staining (10 μm; Invitrogen, Carlsbad, Calif.) was used for counterstaining cell nuclei.

Statistics.

Means±SEM are given where not otherwise indicated. Statistical comparisons between groups of data were performed with SigmaPlot software using a two-tailed unpaired, or paired, where appropriate, Student's t-test to test the null hypothesis. Values of probability of $P<0.05$ are considered to be statistically significant.

Example 1

Development of Polysynaptic Burst Responses in EC L5 Neurons Post SE

In slices from control rats, single presynaptic stimulation to EC L5 elicited a monosynaptic, fast EPSP of up to 20 mV in amplitude in L5 neurons at resting membrane potential (RMP) of ∼−70 mV (FIG. 1A), followed by a fast inhibitory postsynaptic potential (IPSP) whose amplitude varied with the membrane holding potential. In strong contrast, recordings made 3 weeks after SE showed polysynaptic epileptiform activity in response to a single synaptic stimulation, even when stimulation intensity was greatly reduced from values used for the control preparations (FIG. 1B). The polysynaptic burst responses showed little change with variation of the postsynaptic membrane potential by DC injection in a range from −95 to −60 mV, except in firing of action potentials for the more depolarized voltages. In the example shown, the slight delay of the polysynaptic depolarization with weak stimulation allowed the initial EPSP to become clearly evident; and to be seen as only 1-2 mV in amplitude (inset, cell hyperpolarized by negative DC to prevent firing). These weak stimuli reliably elicited polysynaptic burst responses in 10.8% of the neurons tested at 2 weeks (n=37), and in 61.8% (n=34) at 3 weeks (FIG. 1C).

For these determinations, a polysynaptic burst was defined as a post-synaptic response lasting more than 150 ms at half amplitude, elicited from −75 mV<RMP<−68 mV. In control slices such responses were seen only in 1 neuron out of 42 recorded neurons.

Further details of FIG. 1, and the experiment(s) which yielded the data reflected in that figure, are as follows.

FIG. 1: Increased polysynaptic Burst Excitation in EC L5 Neurons Post SE.

A: Postsynaptic response in EC-L5 neuron from untreated rat to single presynaptic stimulus (*, 500 nA, 70 μs). B: Polysynaptic burst response in L5 neuron 3 weeks after SE to a much smaller stimulus (*, 100 nA, 70 μs, see also FIGS. 10 & 11). The primary evoked PSP (box) is shown enlarged in the inset (30 ms×5 mV). For this recording the cell was hyperpolarized by negative DC to prevent firing. C: Bar chart showing percent of EC-L5 neurons responding to a single stimulation with a polysynaptic depolarization. A single stimulus evokes a polysynaptic response in only 2.4% of EC-L5 cells from control rats (n=42), but in 10.8% and in 61.8% of cells from rats 2 (n=37) and 3 weeks after SE (n=34), respectively.

Example 2

GABA$_A$ergic PSPs Become Depolarizing, Post SE

Figure 2:
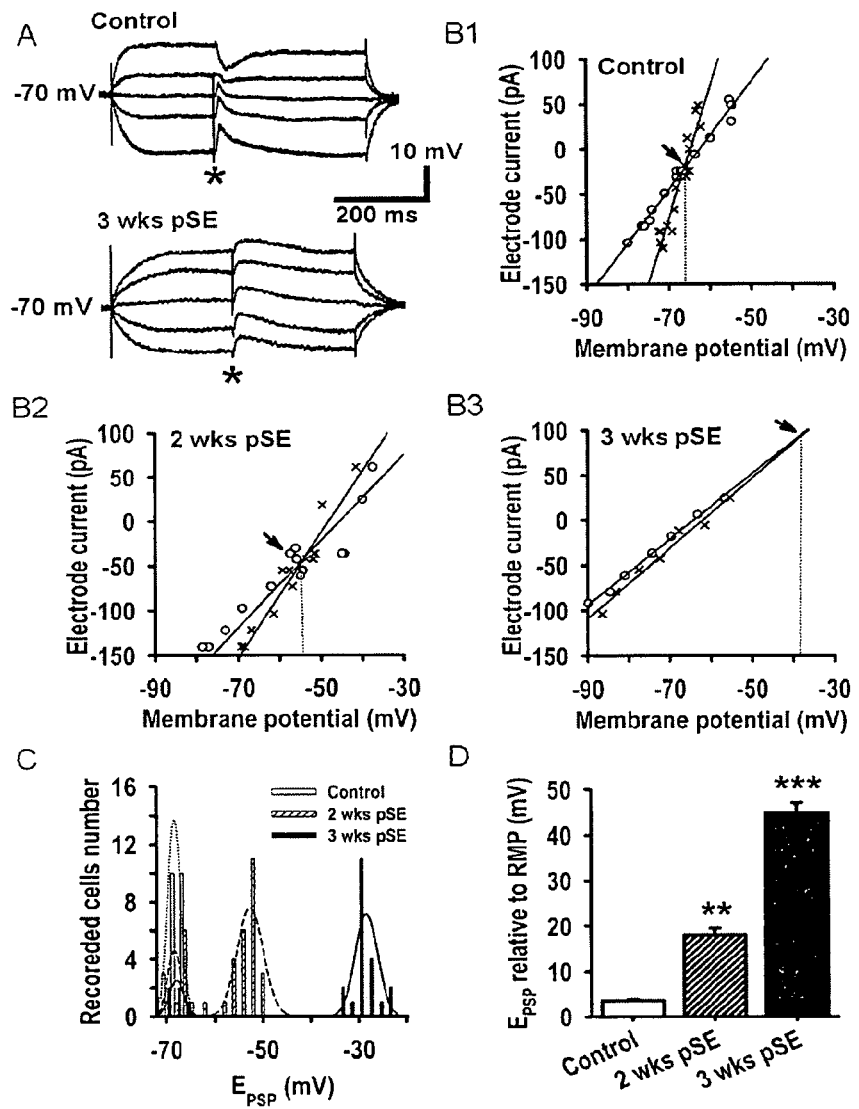
FIG. 2 illustrates a positive shift of the GABA$_A$ergic PSP reversal potential 2 and 3 weeks after SE, as explained in the "Materials and Methods" section and Example 2 hereinafter.

Drawing on existing observations of important changes in $E_{IPSP}$ and Cl$^-$ transporter systems in a subpopulation of subicular neurons with long established TLE (Cohen et al., 2002; de Guzman et al., 2006; Palma et al., 2006; Huberfeld et al., 2007; Munoz et al., 2007; Sen et al., 2007), we looked for ongoing changes in GABAergic transmission at the very early stages of interest here that might promote burst activity. FIG. 2A illustrates monosynaptic GABA$_A$ergic PSPs, during block of glutamate receptors by CNQX (10 μM) and APV (50 μM), that were elicited by field stimulation in EC L5 while cells were held at different steady membrane potentials (see Materials and Methods). The PSP reversal potential ($E_{PSP}$) was determined by plotting the I-V relationships of both the steady membrane potential (FIG. 2B, o's) and peak voltage of the PSP (FIG. 2B, x's), and calculating the linear regressions. The crossover point of membrane potential and PSP linear regressions is the reversal potential (FIG. 2B, arrows). I-V plots for representative neurons from control rats and from rats 2 and 3 weeks post SE illustrate a progressive shift of $E_{(PSP)}$ from −68.3±2.1 mV in control to −52.6±1.8 mV 2 weeks and −34.8±1.4 mV 3 weeks post SE, respectively (FIG. 2, B1-3). When the data were plotted as histograms, we observed two classes of cells in the slices from the treated rats, at both 2 and 3 weeks post SE (FIG. 2C, n=84). In one class, the mean $E_{(PSP)}$ was similar to controls, i.e. <5 mV positive to RMP (23.5% and 19.2% of the total cells analyzed at 2 and 3 weeks, respectively). The other class showed strong shifts (76.5% and 80.8% of recorded neurons at 2 and 3 weeks, respectively). Both classes of cells were observed not only in slices from the same rat, but also within single slices. Pre-sacrifice spontaneous seizures, expected in up to ~25% of rats at 3 weeks post SE (see Methods), could have further shifted $E_{(PSP)}$ in neurons from these rats, thus establishing a subpopulation with more strongly shifted $E_{(PSP)}$. The histogram does not show any sign of such a distinct subpopulation of neurons, indicating that spontaneous seizures did either not occur or did not significantly further shift $E_{(PSP)}$.

The bar graph of population data (FIG. 2D) summarizes the mean PSP reversal potential shift over time, excluding that part of the population where no change occurred ($E_{(PSP)}$=3.6±0.5 mV positive to RMP of −71.9±1.46 mV in control neurons, n=24; 2 weeks after SE $E_{(PSP)}$=18.0±3.6 mV positive to RMP of −70.9±2.8 mV, $t_{56}$=8.3, P=0.006, n=26; three weeks after SE $E_{(PSP)}$=45.1±6.2 mV positive to RMP of −72.9±2.8 mV, $t_{48}$9.81, P=0.0008, n=21). At the 3 week measurement point, 81% and 75% of neurons in the shifting and non-shifting population, respectively, were pyramidal and 19% and 25%, respectively, multipolar neurons. These distributions are not significantly different from the overall distribution of these two cell types in EC L5 (Egorov et al., 2002; Egorov et al., 2003). It is notable that the positive shift at 3 weeks brings the $E_{(PSP)}$ very close to the level of spike initiation. Thus, post SE GABA release may not effectively limit repetitive firing, and might possibly even excite neurons.

The slightly depolarizing IPSP in control neurons, relative to resting membrane potential, may seem puzzling for a condition where apparently only Cl$^-$ outward transport is expressed (see below). The Cl$^-$ reversal potential should be negative to the resting membrane potential (or equal to it when Cl$^-$ outward transport becomes active only after Cl$^-$ influx). However, the GABA$_A$-channels conduct bicarbonate to some extent, about ⅕ of the anion conductance, making the GABA-PSP reversal potential lie between $E_{Cl^-}$ and $E_{HCO_3^-}$ (Bormann et al., 1987). Intracellular energy metabolism generates carbon dioxide that reversibly reacts with water, catalyzed by carbonic anhydrase, to form bicarbonate. This process creates a strong outward gradient for HCO$_3^-$ with a reversal potential as positive as −10 mV (Ben-Ari et al., 2007). This should shift the PSP reversal to a value more positive than $E_{Cl}$ in normal animals (Staley et al., 1995). Also, it is possible that limited expression of Cl$^-$ inward transport could produce a slightly depolarizing PSP reversal potential (see below).

In addition to the reversal potential change, the membrane slope conductance, and the conductance increase during the PSP progressively declined post SE (cf. FIG. 2, B1-3). Resting conductance fell from 5.9±0.7 nS in control to 4.8±0.7 ($t_{12}$=3.66, P=0.032) and 3.6±0.4 nS ($t_{13}$=3.79, P=0.026) 2 and 3 weeks after SE, respectively, probably due to downregulation of leak ion channels (Bernard et al., 2004; Gorter et al., 2006). Similarly, the peak GABA-activated conductance fell from 8.5±0.69 nS in control to 2.1±0.4.3 ($t_{12}$=13.12, P=0.0018) and 0.24±0.07 nS ($t_{13}$=6.16, P=0.0005) 2 and 3 weeks after SE, respectively. This decrease was confirmed with larger GABAergic PSPs elicited by stimulation intensity close to maximum of the input-output relation, and repeated 3 times at 100 Hz, giving a larger undisturbed PSP after the third stimulation for all three groups.

Further details of FIG. 2, and the experiment(s) which yielded the data reflected in that figure, are as follows.

FIG. 2. Positive Shift of the GABA$_A$Ergic PSP Reversal Potential 2 and 3 Weeks after SE.

A: Monosynaptic GABA$_A$ergic PSPs evoked at 5 different membrane potentials in EC L5 neuron from a control (upper traces) and from a rat 3 weeks after SE (lower traces) recorded with a sharp microelectrode. Membrane potential was altered by current application (500 ms pulses) through the microelectrode. Asterisks denote time of presynaptic stimulus. Recordings were performed in the presence of the AMPA/kainate glutamate receptor antagonist CNQX (10 μM) and the NMDA receptor antagonist APV (50 μM). B1,2,3: I-V relationship of prestimulus membrane potential (o) and the absolute value of the GABA$_A$ergic PSP (×) measured 15 ms after stimulation vs. electrode current. Data were obtained using the protocol of part A, fitted with linear regressions. Intersection of membrane potential and PSP plots occurs at the PSP reversal potential ($E_{PSP}$, arrows). C: Histograms showing the number of EC L5 neurons displaying a $GABA_A$ergic reversal potential within a 2 mV range at the 3 time points examined. Envelops (dotted curves) are best Gaussian fits to the 5 obvious populations. In neurons from control rats, the $E_{PSPs}$ Gaussian fit has a median value of ~−69 mV. Neurons from rats both 2 and 3 weeks after SE broke into 2 classes, no $E_{psp}$ shift, and significant shift. At 2 weeks 77% of the neurons had a shifted mean of ~−54 and at 3 weeks 81% displayed a mean shift to ~−28 mV. The non-shifting neurons comprised 23 and 19% of the populations respectively. Their $E_{PSP}$ distribution was indistinguishable from the control group. N=24, 34 and 26 recorded cells for control and 2 and 3 week groups.

D: Mean±SEM of $GABA_A$ergic $E_{PSP}$ relative to resting membrane potential (RMP) for the shifted populations 2 (n=26) and 3 weeks after SE (n=21) demonstrate a progressive depolarizing shift of the reversal potential in comparison with control (n=24, p<0.01, * p<0.001).

Example 3

Increase of NKCC1 mRNA After SE

Figure 3:
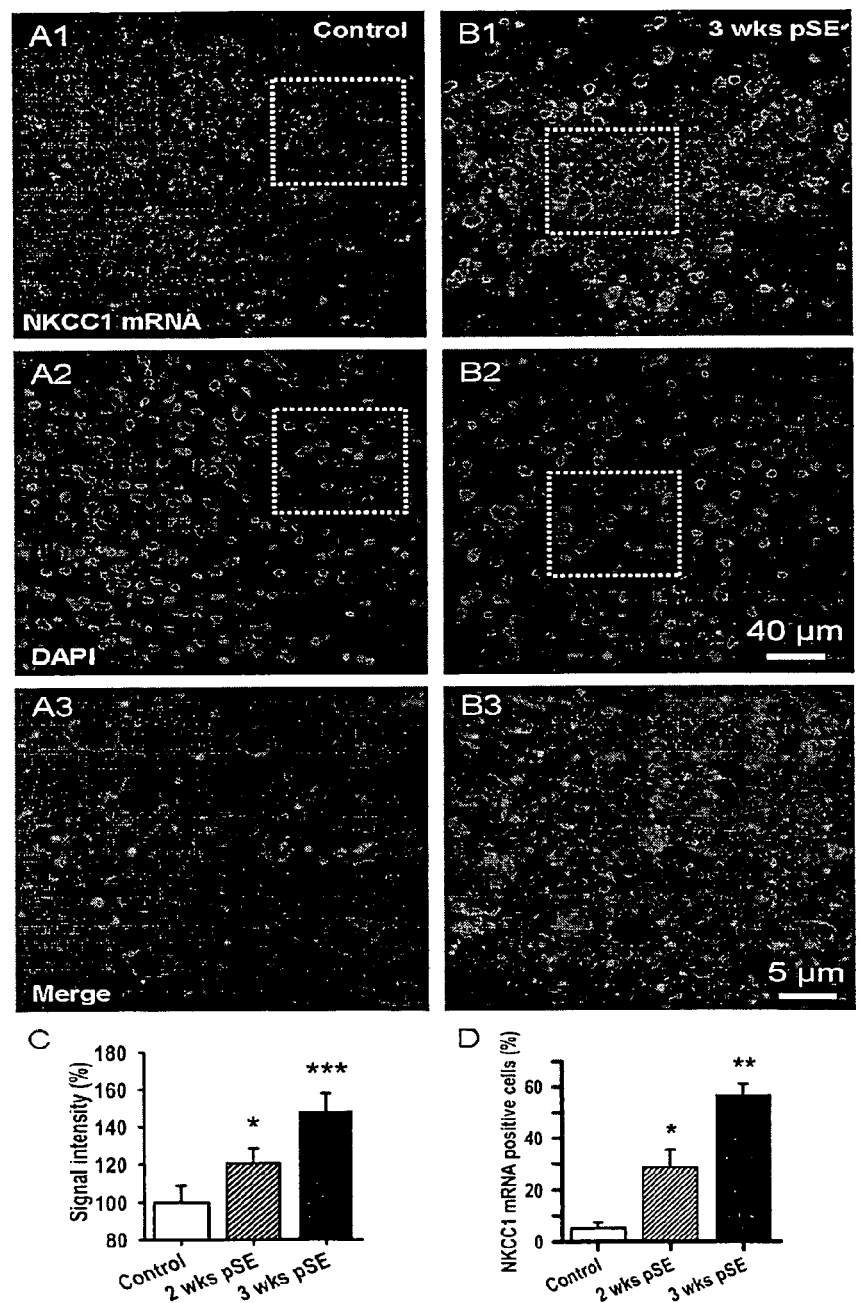
FIG. 3 illustrates that mRNA for NKCC1, a Cl$^-$ inward transporter, progressively increases post SE in EC L5, as determined in the experiment(s) of Example 3.

The strongly depolarizing GABAergic PSP post SE, requires active Cl$^-$ inward transport. However it is known that there is little expression of NKCC1 in adult neurons (Delpire, 2000; Wang et al., 2002). We examined whether NKCC1 mRNA expression is re-established in adult EC L5 neurons during the post SE latent period, recapitulating an early developmental stage (Yamada et al., 2004; Ben-Ari et al., 2007). We found that NKCC1 mRNA fluorescence was very low to absent in EC L5 in control rats (FIG. 3A), in agreement with previous studies. In contrast, at 2 and especially 3 weeks after Li-pilocarpine induced SE, we observed clear NKCC1 staining (FIG. 3B). At 2 weeks post SE, NKCC1 mRNA fluorescence had increased to 237±33.4% of control and to 452±33.5% at 3 weeks (FIG. 3B, E, n=100 ROIs, see Methods, 4 rats in each group, $t_{38}$=2.15, P=0.037 and $t_{49}$=3.54, P=0.0009, respectively). These percentages are somewhat arbitrary given the low expression in controls, but indicate a very large increase in expression. Nucleus counterstaining with DAPI demonstrated no change in cell numbers over the analysis period (12.2±2.7, 12.8±3.4 and 12.5±3.1 nuclei per 500 μm2 for control and 2 and 3 week post SE, respectively, $t_{68}$=−0.49, P=0.62 and $t_{68}$=−2.38, P=0.24, respectively, n=100 ROIs, 4 rats in each group; FIG. 3 A2, B2). Overlay of DAPI and NKCC1 mRNA images shows a primarily perinuclear location of the labeled mRNA (FIG. 3 B2). Analysis of NKCC1 positive cells relative to all cells in the fields, showed a labeling of 5.1±2.1% of the cells in control tissue which increased to 28.5±6.7% and 56.7±4.3% at 2 and 3 weeks post SE, respectively (FIG. 3D, n=100 ROIs, 4 rats in each group, $t_{38}$=3.27, P=0.042 and $t_{49}$=2.71, P=0.0096, respectively.

Further details of FIG. 3, and the experiment(s) which yielded the data reflected in that figure, are as follows.

FIG. 3. mRNA for NKCC1, a Cl$^-$ inward transporter, progressively increases post SE in EC L5.

A, B: Fluorescence in-situ-hybridization shows up-regulation of NKCC1 mRNA 3 weeks after pilocarpine insult in comparison with control (red signal, A1, B1). DAPI nuclear stain indicated no change in cell numbers (blue signal A2, B2). The lower panels, A3 & B3 show magnified, merged views of the areas outlined in A1,2 & B1,2 and illustrate perinuclear localization of NKCC1 mRNA (A3, B3). C: Bar graph showing increase in NKCC1 mRNA post SE. Data were quantified by forming the ratio of the total NKCC1 signal to total fluorescence of the nuclear stain in a given ROI. These ratios were then normalized to the values from control rat (mean±SEM, n~100 ROIs for 4 rats in each group, * p<0.01, *** p<0.001). D: Mean number of NKCC1 mRNA-positive cells, expressed as % of nuclei number determined from DAPI staining (mean±SEM, n~300 cells for 4 rats in each group, * p<0.05, ** p<0.01).

Example 4

Increase of NKCC1 Protein

Figure 4:
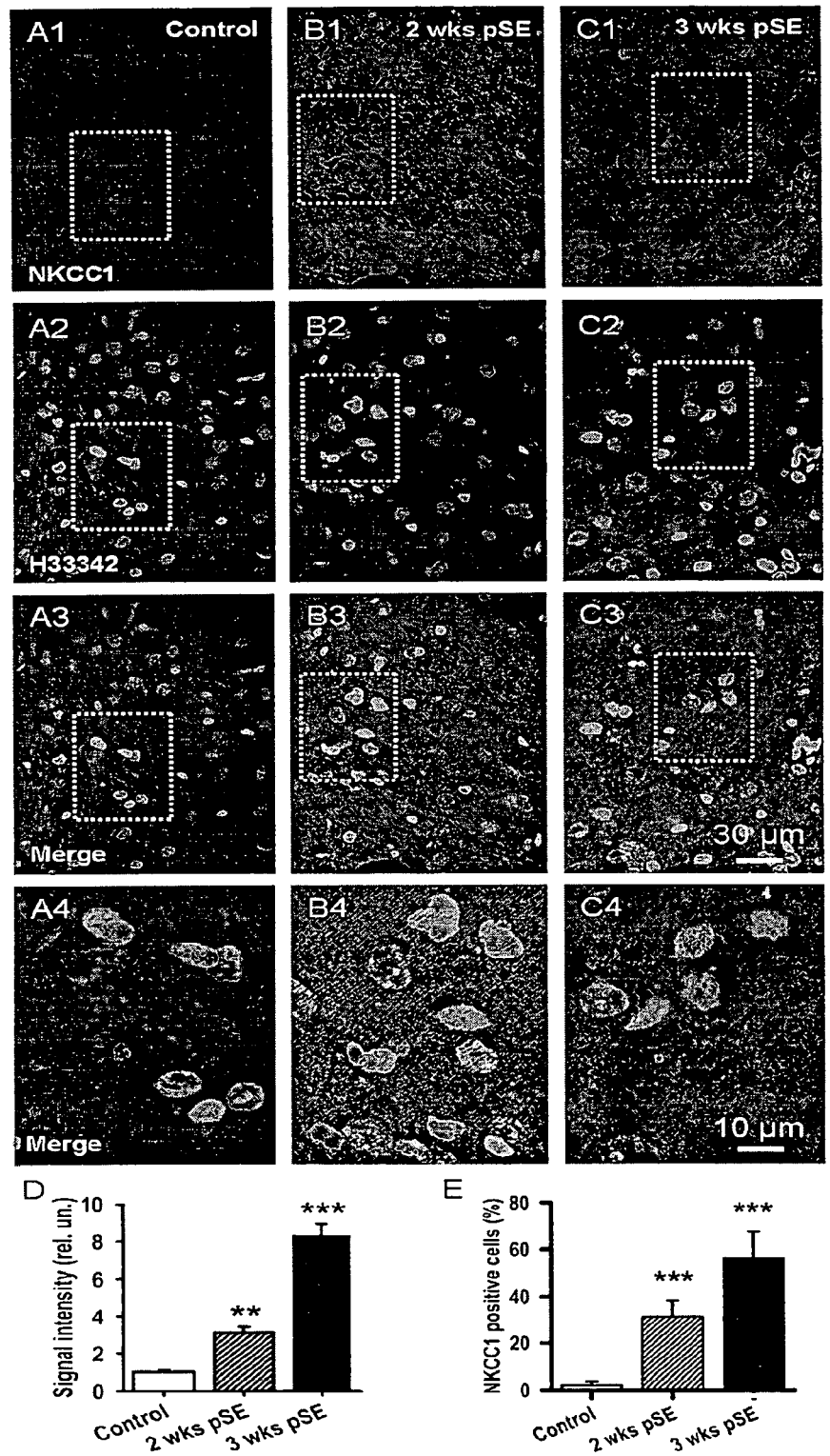
FIG. 4 illustrates that in the experiment of Example 4, NKCC1 protein was also upregulated

To analyze protein level changes of NKCC1 that occurred during the latent period we performed fluorescence immunohistochemistry. These data were obtained with the Chemicon NKCC1 antibody, as shown in FIG. 4, and demonstrate a progressive increase of NKCC1 protein from 2 to 3 weeks after SE, whereas in slices from control rats, there was very little specific signal (FIG. 4 A-C). Similar results were obtained with the MabT4 NKCC antibody. Superposition of stained nucleus images (Hoechst 33342) onto NKCC1 images revealed, particularly at 3 weeks post SE, a preferential perinuclear and somatic location of NKCC1, suggesting significantly increased neuronal protein synthesis (FIG. 4 B3, C3 and, at higher magnification, B4, C4). Again, the number of Hoechst stained nuclei did not show significant differences between the three rat groups (85.3±5.3 in control vs. 97.7±3.4 two weeks, and 86.0±4.9 three weeks post insult, 4 rats, $t_{20}$=−1.33, P=0.20 and $t_{18}$=−2.35, P=0.81, respectively, n=100 ROIs, 4 rats in each group). FIG. 4 D shows that average NKCC1 fluorescence intensities from cell bodies were some 350% and 860%, of control background fluorescence at 2 and 3 weeks respectively (n=100 ROIs, 4 rats in each group, $t_{64}$=5.32, P=0.0006 and $t_{51}$=4.56, P=0.0008, respectively). In the neuropil average NKCC1 fluorescence intensities were 123±21% and 222±45% of control background fluorescence at 2 and 3 weeks respectively, suggesting a delayed increase of NKCC1 protein in dendrites (n=100 ROIs, 4 rats in each group, $t_{32}$=4.25, P=0.025 and $t_{36}$=5.31, P=0.008, respectively). In terms of individual cells, 31.2±6.9% and 56.3±11.2% of cell bodies were clearly positive for NKCC1 2 and 3 weeks post SE, respectively, whereas none was evident in control (FIG. 4 E, n=100 ROIs, 4 rats in each group, $t_{42}$=11.24, P=0.0009 and $t_{37}$=7.12, P=0.0007, respectively).

Figure 5:
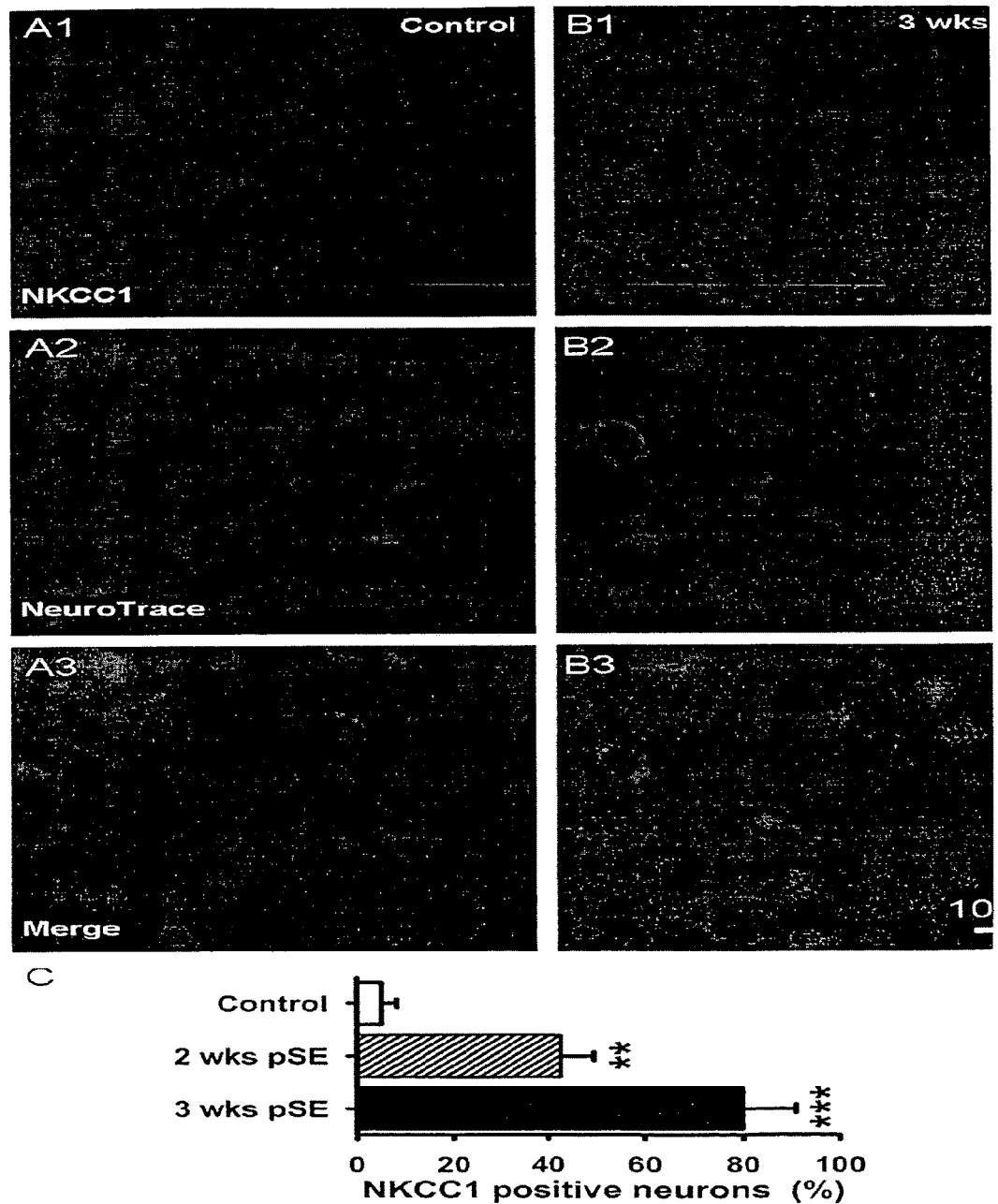
FIG. 5 illustrates that EC L5 neurons increase expression of NKCC1 protein post SE, as determined in the experiment(s) of Example 4.

In FIG. 5 neuron-specific NeuroTrace counterstaining was used and showed that 77.1±8.1% of neurons had become NKCC1 positive 3 weeks after insult (control tissue: 3.0±1.3%, n=3 rats in each group, $t_{21}$3.78, P=0.008 and $t_{33}$=4.23, P=0.001, respectively). The higher percentage of NKCC1 positive neurons than of NKCC1 positive cells suggests that NKCC1 is mostly upregulated in neurons. NeuroTrace positive cell number was also stable over the experimental period (35.4±7.2 in control vs. 37.1±6.4 two weeks, and 36.6±6.7 three weeks post insult, 3 rats in each group, $t_{12}$=−0.51, P=0.6 and $t_{16}$=−0.30, P=0.8, respectively), indicating that the stable H33342 cell count was not the result of compensating neuron loss and glial cell increase. The gradual increase in NKCC1 expression and the percentage of positive neurons is well suited to explain the concurrent progressive depolarizing shift in $GABA_A$-PSP reversal potential.

Further details of FIGS. 4 and 5, and the experiment(s) which yielded the data reflected in those figures, are as follows.

FIG. 4. NKCC1 protein is also upregulated. A, B, C: Fluorescence immunohistochemistry demonstrates progressive increase in expression of NKCC1 protein from 2 to 3 weeks after SE in EC L5 (red signal, A1, B1, C1). Hoechst 33342 nuclei counterstain shows stable cell number (A2, B2 and C2, green signal). Merged views of the upper panel sets (A3, B3, C3) illustrate the pervasive increase in expression. The boxed regions of these panels are shown enlarged below to better illustrate perinuclear and somatic location of NKCC1 (A4, B4, C4). D: Bar graph showing increase in NKCC1 protein post SE. Data were quantified by forming the ratio of the total NKCC1 signal to total fluorescence of the nuclear stain in a given ROI. These ratios were then normalized to the values from control rat (mean±SEM, 3 rats,  $p<0.01$, * $p<0.001$). E: Mean number of NKCC1 positive cells, expressed as % of nuclei number (H33342, mean±SEM, 3 rats, *** $p<0.01$).

FIG. 5. EC L5 neurons increase expression of NKCC1 protein post SE.

A, B: Fluorescence immunohistochemistry demonstrates strong expression of NKCC1 protein 3 weeks after SE in EC L5 (red signal, A1, B1). Neuron-specific NeuroTrace counterstain shows stable cell number (A2, B2, green signal). Overlay views illustrate perinuclear and somatic location of NKCC1 (A3, B3). Here, neurons throughout a 60 μm thick tissue block are shown. C: Mean of NKCC1 positive neurons, in % of NeuroTrace positive cells, progressively increases 2 and 3 weeks after pilocarpine-evoked SE in EC L5 (mean±SEM, 3 rats, *** $p<0.01$).

Example 5

Progressive Decrease of KCC2 mRNA

The demonstrated upregulation of NKCC1 suggests active Cl⁻ uptake. Normal Cl⁻ extrusion by the neuronal KCl cotransporter KCC2 (Ben-An et al., 2007) would compete with, and more or less short-circuit this Cl⁻ uptake. If KCC2 expression is maintained it would limit the effectiveness of Cl⁻ uptake and waste metabolic energy. To see if this is the case we studied expression of KCC2 mRNA.

Figure 6:
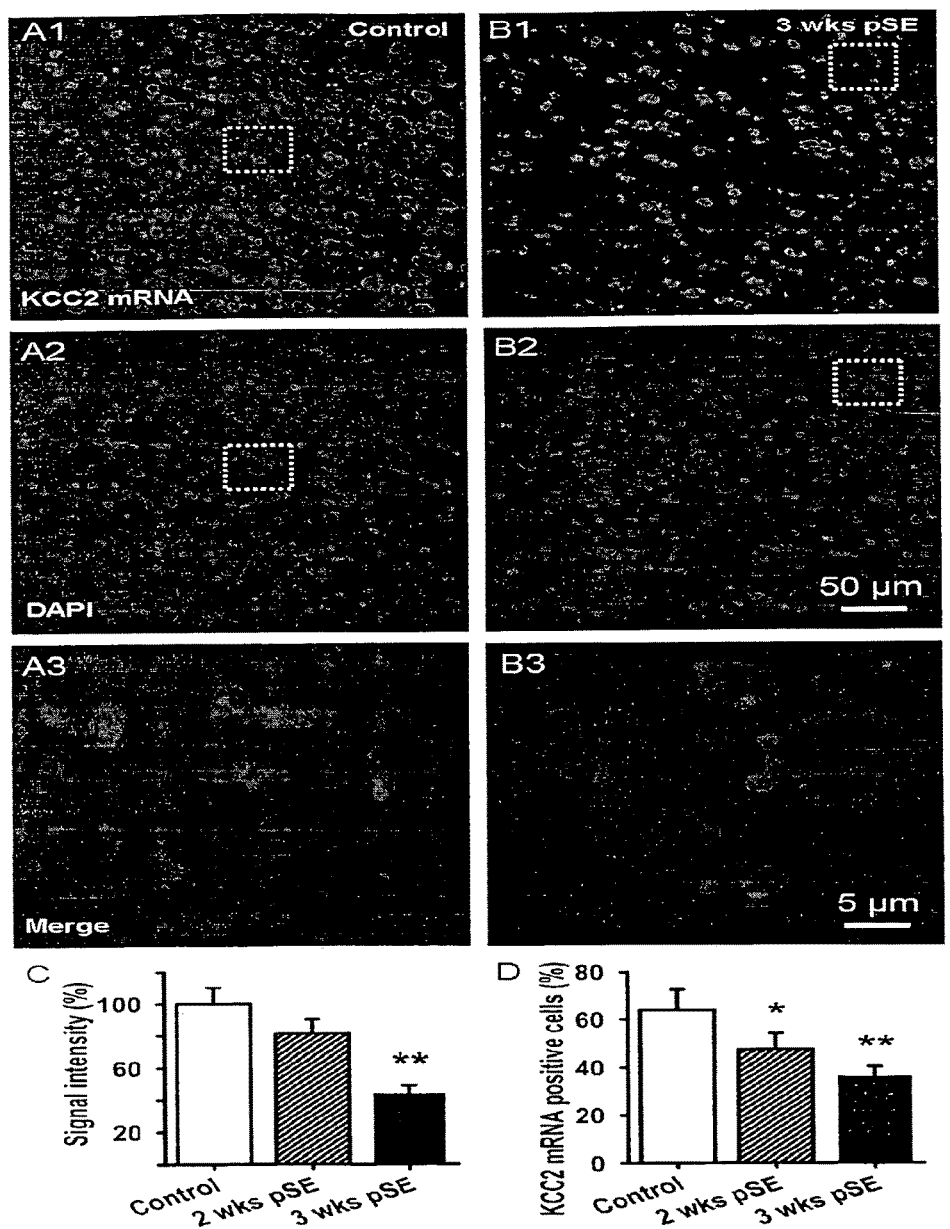
FIG. 6 illustrates that mRNA for KCC2, a neuronal Cl$^-$ outward transporter, progressively decreases post SE in EC L5, as determined in the experiment(s) of Example 5.

As above, we assessed the expression levels of KCC2 mRNA in L5 neurons by fluorescence in situ hybridization. FIG. 6 shows that KCC2 mRNA was expressed abundantly in control animals (A1) while 3 weeks after SE, expression of KCC2 mRNA was strongly diminished (B1). Staining of cell nuclei with DAPI did not show significant differences between the 3 time points (11.9±2.9, 12.3±3.8 and 12.1±3.2 nuclei per 500 μm² respectively, $t_{24}=-0.36$, $P=0.17$ and $t_{24}=-0.41$, $P=0.24$, respectively, FIG. 6: A2, B2). The merged fluorescence images (FIG. 6: A3, B3) show that KCC2 mRNA is localized in the nuclear and perinuclear regions of the cells.

KCC2 mRNA fluorescence, normalized to control, showed a progressive decrease of KCC2 mRNA expression 2 and 3 weeks after SE to 81∓8.3 and 44±7.8% of control level, respectively (FIG. 6 C, n~100 ROIs, see Methods, 4 rats in each group, $t_{62}=1.95$, $P=0.08$ and $t_{62}=2.34$, $P=0.0095$, respectively). Similarly, the proportion of EC L5 cells expressing KCC2 mRNA (at least 2 red spots around the nucleus as in FIGS. 6 A3 & B3), relative to the number of nuclei, decreased from 63.9±8.5% of EC L5 cells in control animals to 47.3±6.7 and 36.3±4.3% of total cell number 2 and 3 weeks after SE, respectively (FIG. 6 D, mean±SEM, n~300 cells for 4 rats in each group, $t_{34}=3.14$, $P=0.045$ and $t_{28}=4.21$, $P=0.007$, respectively).

Further details of FIG. 6, and the experiment(s) which yielded the data reflected in that figure, are as follows.

FIG. 6. mRNA for KCC2, a neuronal Cl⁻ outward transporter, progressively decreases post SE in EC L5, A, B KCC2 mRNA expression detected by fluorescence in-situ-hybridization shows down-regulation of KCC2 mRNA 3 weeks after pilocarpine induced SE in comparison with control (A1, B1, red signal). DAPI nuclear stain indicated no change in cell numbers (A2 & B2: blue signal). Merged magnified views of the areas outlined in A1,2 & B1,2 illustrate perinuclear localization of KCC2 mRNA (A3 & B3). C: Bar graph showing decrease in KCC2 mRNA post SE. Data were quantified by forming the ratio of the total KCC2 signal to total fluorescence of the nuclear stain in a given ROI. These ratios were then normalized to the values from control rat (mean±SEM, n-100 ROIs for 4 rats in each group, ** $p<0.01$). D: Mean number of KCC2 positive cells, expressed as % of nuclei number (DAPI, mean±SEM, n~300 cells for 4 rats in each group, * $p<0.05$ and ** $p<0.01$, respectively).

Example 6

Progressive Decrease of KCC2 Protein

Figure 7:
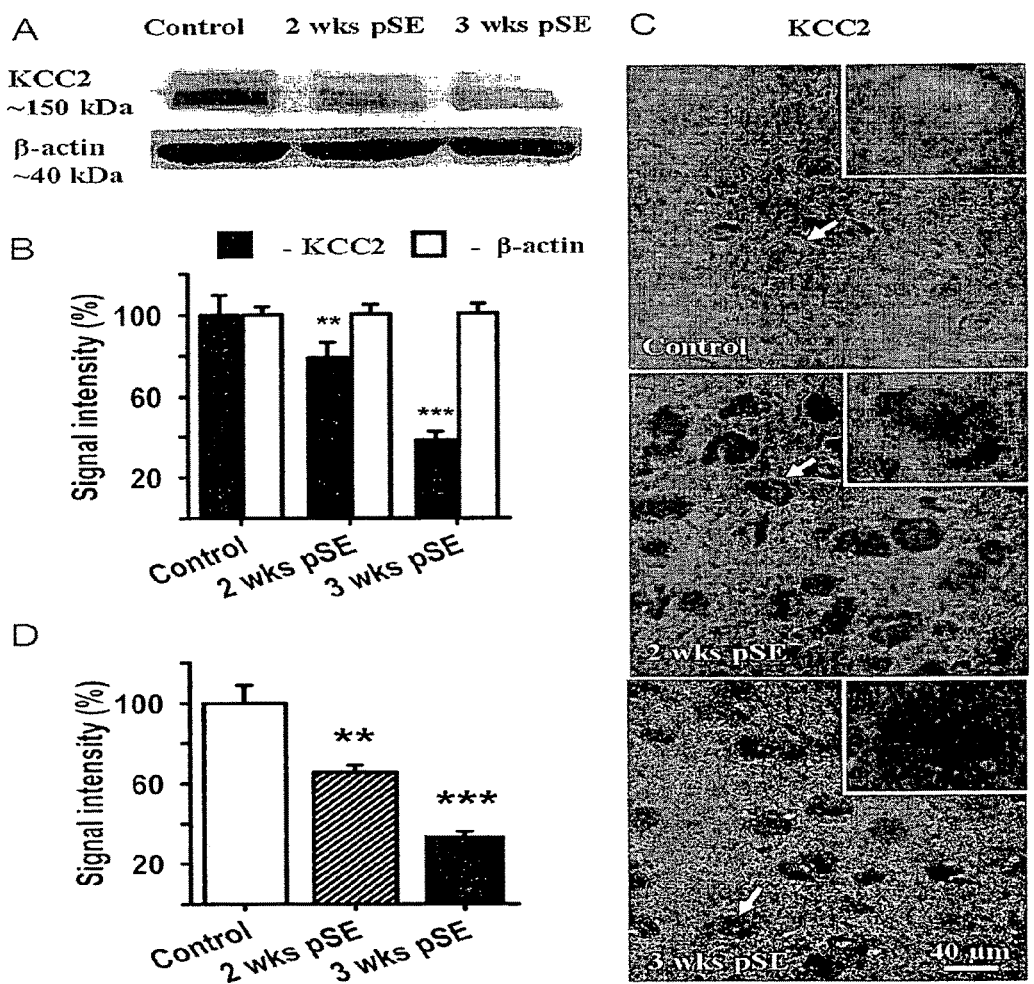
FIG. 7 illustrates that KCC2 protein also decreases post SE, as determined in the experiment(s) of Example 6.

We also examined KCC2 protein levels in EC L5 from control and post SE rats using Western blot and single cell analysis. The results, shown in FIG. 7 A, B, illustrate a significant reduction of KCC2 protein 2 and 3 weeks after SE to 78.8±7.5 and 38.1±4.3% of control levels, respectively (mean±SEM, n=5 rats, $t_2=2.17$, $P=0.01$ and $t_{18}=4.6$, $P=0.0006$, respectively). Using fluorescence immunohistochemistry we also studied the distribution of KCC2 protein and its loss after treatment (FIG. 7 C). In control rats KCC2 immunoreactivity was detected as densely packed perisomatic fluorescence (FIG. 7 C, top panel, and inset) on top of a diffuse neuropil signal Two and 3 weeks post SE, KCC2 immunofluorescence had gradually decreased in the neuronal cell bodies (FIG. 7 C, D) with a weak discrete fluorescence remaining in the perisomatic areas of the EC L5 neurons (FIG. 7 C, middle and lower panel, and insets). Somatic immunofluorescence for KCC2 decreased to 66±3.5 and 34±1.9% of control level 2 and 3 week after SE, respectively (FIG. 7 D, mean±SEM, n=100 ROIs from 4 rats, $t_{34}=7.85$, $P=0.007$ and $t_{41}=6.39$, $P=0.00006$, respectively).

In the neuropil, the KCC2 signal decrease was more delayed. Here, the KCC2 signal decreased to 96±4.1% and 60±4.4%, at 2 and 3 weeks respectively. Roughly estimating a 1:1 ratio for soma versus neuropil volume, total KCC2 immunofluorescence changes are in good agreement with the Western Blot data. To establish that neurons were not dying and replaced by glia, the neuron-specific fluorescent NeuroTrace Stain was used for counterstaining. These stainings showed stable number of neurons (157.6±6.5 in control vs. 154.6±21.3 three weeks post insult, 3 rats, $t_{26}=2.34$, $P=0.44$) and that the KCC2 signal was highly specific for neurons (>95% of KCC2 positive cells were NeuroTrace positive). Interestingly, in the high-dose pilocarpine model, there is also evidence for an early, functional downregulation of KCC2 in the downstream dentate gyrus that compromises the gatekeeper function of this structure for spread of epileptiform activity from the EC into the hippocampus (Pathak et al., 2007). Concurrent with the compromise in this gatekeeper function, there is evidence for epileptiform EEG activity in vivo (El-Hassar et al., 2007).

Further details of FIG. 7, and the experiment(s) which yielded the data reflected in that figure, are as follows.

FIG. 7. KCC2 protein also decreases post SE. A: Western blot KCC2 bands (~150 kDa) show significant gradual down-regulation of KCC2 in an EC L5 region of rats 2 (2 wks pSE) and 3 weeks (3 wks pSE) after pilocarpine induced SE in comparison with control. β-actin (~40 kDa) served as a loading control. B: Average optical densities, extracted from blots as in A, in % of control (mean±SEM, n=5,  p<0.01, * p<0.001). These data are in excellent agreement with the mRNA and IPSP reversal potential data. C: Immunohistochemistry shows a gradual decrease of KCC2 protein 2 and 3 weeks after pilocarpine induced SE, most prominent in somata. The white outlined boxes in each panel show a magnified view of the cells identified by white arrows in each panel. D: Bar graph showing decrease in average immunohistochemistry KCC2 signals post SE, normalized to control. (mean±SEM, n~100 ROIs for 4 rats in each group,  p<0.01, * p<0.001).

Example 7

Early changes in NKCC1 and KCC2 are specific to EC L5

Figure 8:
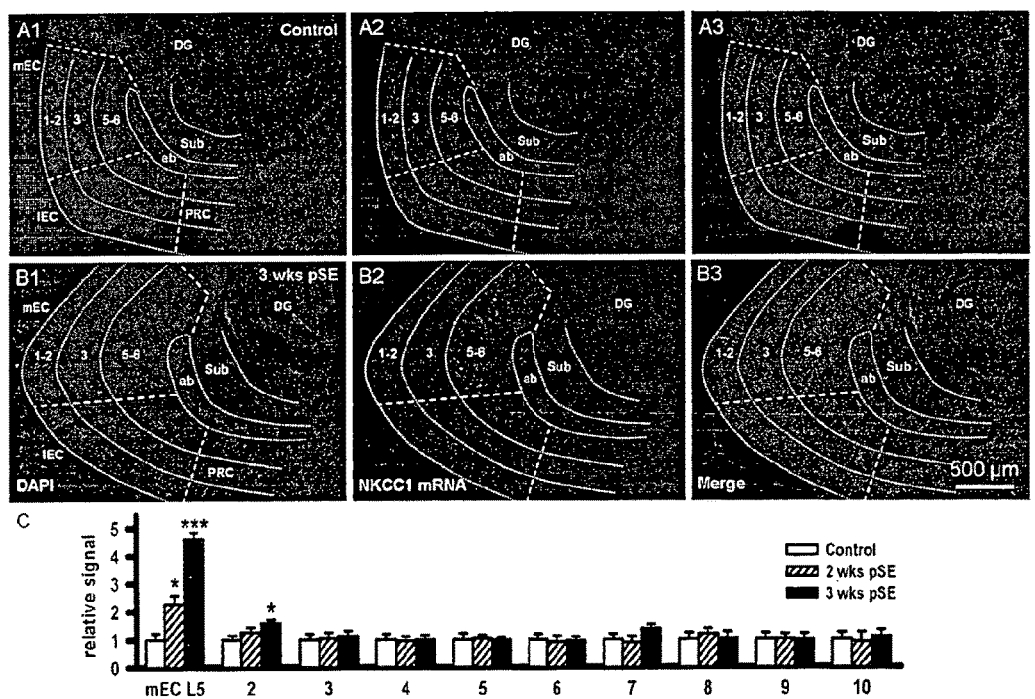
FIG. 8 illustrates that mRNA for NKCC1 does not increase in other cortical regions, as determined in the experiment(s) of Example 7.

The high amplitude EEG spiking that occurs during SE might well be sufficient to trigger the progressive changes in NKCC1 and KCC2 expression seen in EC L5 in other cortical areas, including the hippocampus and subiculum. We therefore extended our analysis to include the superficial layers of the EC, as well as subiculum, dentate gyrus, and perirhinal cortex. FIG. 8 A,B show in a low magnification overview, the expression of NKCC1 mRNA in the deep EC 3 weeks after SE, while superficial layers, subiculum, dentate gyrus and perirhinal cortex show no expression. The plot of mean values of fluorescence from these areas (FIG. 8C, from higher magnification images, and normalized to controls) demonstrates this highly specific expression of NKCC1 mRNA in the deep medial EC, and, to a much weaker extent, in the deep lateral EC (columns 2), while all other regions tested negative (columns 3-10).

Figure 9:
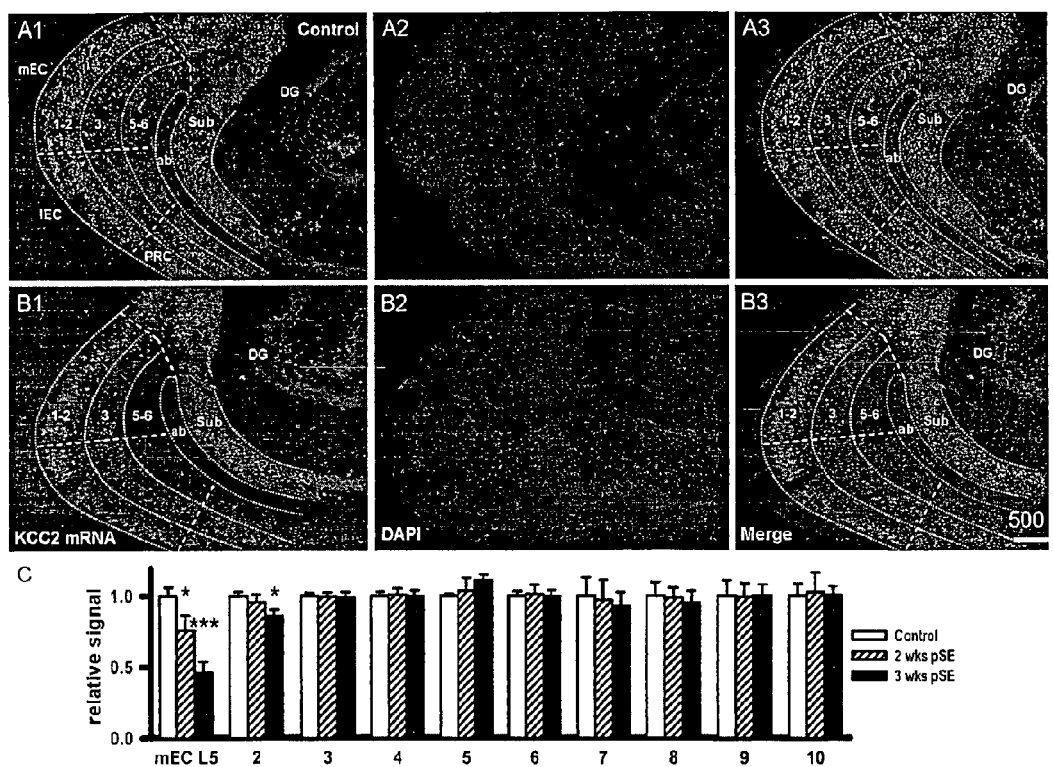
FIG. 9 illustrates that mRNA for KCC2 decreases only in deep EC, as determined in the experiment(s) of Example 7.

The same specificity was observed in the corresponding studies of KCC2 expression. The overview in FIG. 9 A,B shows downregulation of KCC2 mRNA 3 weeks after SE specifically in the deep EC, particularly in the medial part. The quantitative analysis of mean fluorescence demonstrates ongoing downregulation of KCC2 mRNA in the deep mEC by 56±7.8% (3 weeks post SE, $t_{62}$=2.34, P=0.0095) and in the deep lateral EC by 14±4.5% (3 weeks post SE, $t_{62}$=2.41, P=0.039), whereas superficial layers of the EC, as well as subiculum, dentate gyrus, and perirhinal cortex do not show any significant changes (FIG. 9C).

A further important outcome of the extended analysis is that there is no significant early neuronal loss in L3 following the "low dose pilocarpine—Diazepam 1 hour after SE onset" protocol used here, as opposed to "Diazepam administration>2 hour after SE onset" protocols (Du et al., 1995; Kobayashi et al., 2003). First, the absence of significant changes of KCC2 mRNA in EC L3 indicates that L3 pyramidal neurons have not died up to 3 weeks post SE in our rats. Second, neuron survival was confirmed in NeuroTrace stainings that showed stable neuron counts in L3 (114±14.2, 112±18.1 and 116±15 neurons in Control and 2 and 3 weeks after SE, respectively, $t_{10}$=−0.18, P=0.86 and $t_{10}$=−0.77, P=0.46, respectively, 3 rats).

Further details of FIGS. 8 and 9, and the experiment(s) which yielded the data reflected in those figures, are as follows.

FIG. 8. mRNA for NKCC1 does not increase in other cortical regions.

A, B: Fluorescence in-situ-hybridization studies for NKCC1 mRNA showing the brain region encompassing medial (mEC) and lateral EC (lEC), angular bundle (ab), subiculum (Sub), dentate gyrus (DG), and perirhinal cortex (PRC): A, control slice; B, slice taken 3 weeks post SE. Left panels show DAPI staining of the region overlayed with rough outlines of the component areas (A1, B1). Middle panels show NKCC1 signal. In control, there is little to none while 3 weeks after SE signal is apparent in mid EC L5-6 but nowhere else (A2, B2). Images are merged in the right hand panels (A3, B3, for high power images see FIG. 3). C: Bar graph showing increase in NKCC1 mRNA only in deep EC post SE (mEC L5, $t_{54}$=2.15, P=0.037 and $t_{54}$=3.54, P=0.0009, respectively) and lateral EC L5 labeled #2 ($t_{54}$=1.02, P=0.12 and $t_{54}$=1.28, P=0.047, respectively), but no significant changes occurred in mEC L3 (#3, $t_{54}$=0.93, P=0.24 and $t_{49}$=0.42, P=0.34, respectively), lEC (#4, $t_{54}$=0.27, P=0.86 and $t_{54}$=0.24, P=0.094, respectively), mEC L1-2 (#5, $t_{54}$=−1.25, P=0.32 and $t_{54}$=0.34, P=0.23, respectively), lEC L1-2 (#6, $t_{54}$=1.24, P=0.078 and $t_{54}$=0.52, P=0.27, respectively), subiculum (#7, $t_{54}$=1.54, P=0.49 and $t_{54}$=1.67, P=0.063, respectively), dentate gyrus (#8, $t_{54}$=0.45, P=0.098 and $t_{54}$=−1.35, P=0.26, respectively), deep perirhinal cortex (#9, $t_{54}$=0.53, P=0.47 and $t_{54}$=2.01, P=0.48, respectively) and PRC L1-3 (#10 $t_{54}$=−1.36, P=0.81 and $t_{54}$=0.28, P=0.81, respectively; data extracted from higher magnification images).

FIG. 9. mRNA for KCC2 decreases only in deep EC. A, B: Fluorescence in-situ-hybridization studies for KCC2 mRNA showing the brain region encompassing medial (mEC) and lateral EC (lEC), angular bundle (ab), subiculum (Sub), dentate gyrus (DG), and perirhinal cortex (PRC): A, control slice; B, slice taken 3 weeks post SE. Left panels show KCC2 staining of the region, overlayed with rough outlines of the component areas (A1, A2). In control, there is ubiquitous expression while 3 weeks after SE signal has disappeared in EC L5-6, but nowhere else. Middle panels show DAPI staining of the region (A2, B2). Images are merged in the right hand panels (A3, B3, for high power images see FIG. 6). C: Bar graph showing decrease in KCC2 mRNA only in deep EC post SE (mEC L5, $t_{62}$=1.95, P=0.082 and $t_{62}$=2.34, P=0.0095, respectively), and lateral EC L5 labeled #2 ($t_{62}$=1.86, P=0.093 and $t_{62}$=2.41, P=0.039, respectively), but no significant changes occurred in mEC L3 (#3, $t_{62}$=0.34, P=0.32 and $t_{62}$=−1.22, P=0.51, respectively), lEC (#4, $t_{62}$=−0.25, P=0.17 and $t_{62}$=0.24, P=0.36, respectively), mEC L1-2 (#5, $t_{62}$=1.06, P=0.85 and $t_{62}$=0.43, P=0.62, respectively), lEC L1-2 (#6, $t_{62}$=−0.45, P=0.68 and $t_{62}$=0.15, P=0.39, respectively), subiculum (#7, $t_{62}$=−1.01, P=0.098 and $t_{62}$=1.84, P=0.065, respectively), dentate gyrus (#8, $t_{62}$=1.05, P=0.77 and $t_{62}$=−2.03, P=0.49, respectively), deep perirhinal cortex (#9, $t_{62}$=1.33, P=0.28 and $t_{62}$=−1.52, P=0.53, respectively) and PRC L1-3 (#10, $t_{62}$1.12, P=0.085 and $t_{62}$=0.36, P=0.14, respectively; data extracted from higher magnification images).

Example 8

Cl⁻ Transport Block Inhibited Burst Activity

Figure 10:
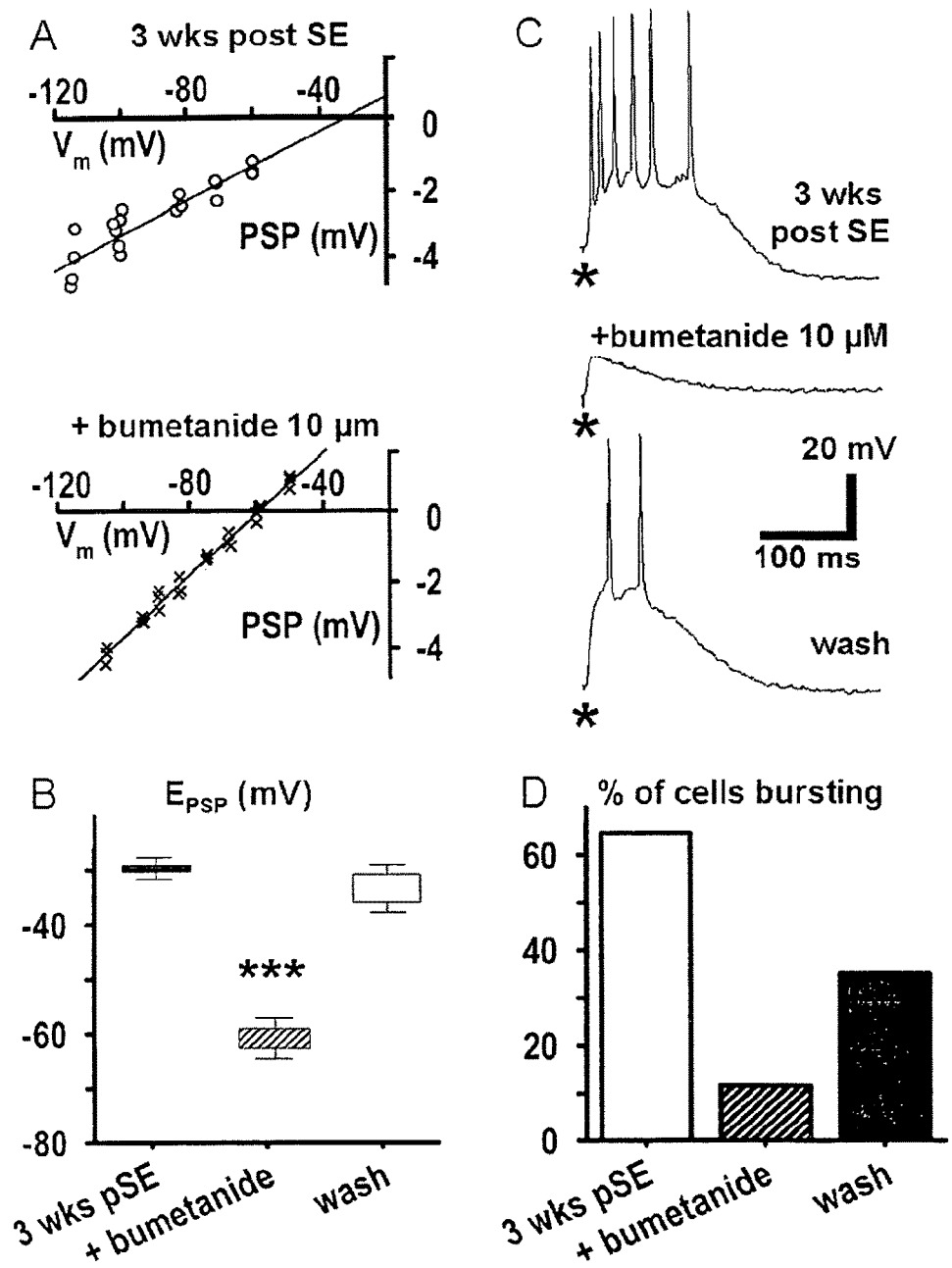
FIG. 10 illustrates that the NKCC1 inhibitor bumetanide partially restores E(PSP), and suppresses polysynaptic excitation, as determined in the experiment(s) of Example 8.

To explore the functional role of NKCC1 upregulation for the shift in $E_{IPSP}$ and the increase in polysynaptic burst responses post insult we employed bumetanide, a diuretic that acts via blockade of Cl⁻ transporters, and is more effective in blocking NKCC vs. KCC transporters (Russell, 2000; Sung et al., 2000; Hammert et al., 2002; Beck et al., 2003). Here its lack of absolute specificity is compensated by 1) the demonstrated strong down-regulation of KCC2 and 2) the fact that only Cl⁻ inward transport can shift $E_{Cl}$ positive to RMP. Block of residual KCC2 activity will not prevent a strong hyperpolarizing shift of $E_{Cl}$ during block of NKCC1. FIG. 10 A shows plots of PSP amplitude, 3 weeks post SE, against membrane voltage, demonstrating that the depolarizing shift in $E_{(PSP)}$ disappeared after a 20 min superfusion with bumetanide (10 μM). This corresponds to a passive redistribution of Cl⁻ across the membrane. FIG. 10 B shows an average PSP reversal potential relative to RMP (∼−72 mV) for EC L5 neurons 3 weeks post SE of more than +40 mV in normal recording condition, reduced to only +10 mV in the presence of bumetanide (absolute voltage average $E_{(PSP)}$ was −29.7±2.3 mV in control conditions, −60.9±4.1 mV in the presence of bumetanide ($t_{24}$=2.26, P=0.00009), and −34.2±3.4 mV during washout of bumetanide, n=5, $t_{24}$=1.52, P=0.0057 vs. bumetanide).

If disinhibition, or even excitation, secondary to the depolarizing shift of $E_{(PSP)}$ is crucial for the occurrence of polysynaptic burst responses in the post SE latent period, then restoring the reversal potential by bumetanide should also block polysynaptic burst responses. FIG. 10 C demonstrates that, indeed, perfusion with bumetanide (10 μM) effectively inhibited polysynaptic responses to single shock stimulation. After recording the strong polysynaptic burst response shown in the top panel of FIG. 10 C, bumetanide superfusion was begun, and by 20 min, burst discharge was strongly attenuated (middle trace). With washout of bumetanide for 30 minutes the strong polysynaptic response was restored (lower trace). On average, bumetanide reduced the number of neurons with a polysynaptic response from 64.8% (9 neurons out of a total of 14) to 11.6% (2/14) of cells from rats 3 weeks after pilocarpine insult. Washout of bumetanide for 30 min restored the number of neurons responding to 35.1% (5/14, FIG. 10 D). The response duration at half-maximal amplitude decreased in bumetanide by 36±9% of the control response ($t_{13}$=13.8, P=0.0000000004), and recovered to 75±11% during washout ($t_{13}$=−5.07, P=0.0002 vs. bumetanide).

Further details of FIG. 10, and the experiment(s) which yielded the data reflected in that figure, are as follows.

FIG. 10. The NKCC1 inhibitor bumetanide partially restores $E_{(PSP)}$, and suppresses polysynaptic excitation. A: Plots of PSP amplitude against membrane potential before (top, open circles) and after a 20 min exposure to bumetanide (bottom, crosses) of an EC L5 neuron from a rat 3 weeks after SE demonstrate a hyperpolarizing shift of PSP reversal potential. Data were obtained from protocols shown in FIG. 2A. The $E_{(PSP)}$ shifts from −29.7 mV to −60.9 mV. Measurements were made during block of EPSPs by CNQX (10 μM) and APV (50 μM). B: Population data showing that the positive-shifted $GABA_A$-PSP reversal potential is strongly and reversibly repolarized by bumetanide (mean±SEM, n=3, *** p<0.001). C: Top record shows that the polysynaptic response to a single stimulus (100 nA) observed 3 weeks post SE is blocked by bumetanide (middle trace) but shows recovery with 30 minutes washout of the drug (bottom trace). D: Population data showing that bumetanide decreases the % of EC-L5 neurons 3 weeks post SE exhibiting a polysynaptic depolarization in response to a single stimulation from 64.8% to 11.6% (n=14). This number recovered to 35.1% after a 30 min washout of bumetanide for 30 minutes.

Example 9

$GABA_A$ergic Excitation Has Minor Effect on Bursts

The depolarizing shift in PSP reversal potential would lead to both, disinhibition and direct GABAergic excitation of L5 neurons. We examined the role of direct excitation in burst responses by blocking $GABA_A$ergic excitation with picrotoxin. Unlike bumetanide, picrotoxin (100 μM) had only modest effects on polysynaptic burst discharge 3 weeks post SE (FIG. 11 A1, A2; in picrotoxin we observed also spontaneous bursts; only evoked bursts recorded >5 s after a spontaneous burst were analyzed; these bursts were apparently not affected by a preceding spontaneous burst). In the population of cells studied, picrotoxin reduced the number of spikes in polysynaptic burst responses from 9.8±0.8 to 7.9±0.7 at 3 weeks post SE (FIG. 11C, n=8 neurons, $t_{24}$=2.26, P=0.000089). When ten of such responses from the same cell were averaged, it was found as in FIG. 11 B1, B2, that picrotoxin reduced action potential amplitudes in the averaged burst responses by 10.5±3.4%, suggesting an increased variability in the timing of action potentials after stimulation (n=8, p=0.094). Thus, the presence of GABAergic excitation apparently increased timing precision of firing in the network, probably due to an overall increase in excitability, rather than direct excitation, as GABAergic transmission may be delayed due to being downstream of interneuron excitation. By contrast to the modest effect of picrotoxin alone, addition of CNQX (10 μM) plus APV (50 μM) to the ACSF/picrotoxin saline almost completely blocked the synaptic responses (−95.9±0.26%, $t_7$=−10.05, P=0.00002), demonstrating that the bursts were mediated primarily by polysynaptic glutamatergic transmission (FIG. 11 A3, B3; in CNQX and APV, with no picrotoxin, monosynaptic PSPs were evoked, as shown in FIG. 2A). There was a trend toward reduction of burst duration in picrotoxin which did not reach statistical significance (FIG. 11D).

Further details of FIG. 11, and the experiment(s) which yielded the data reflected in that figure, are as follows.

Figure 11:
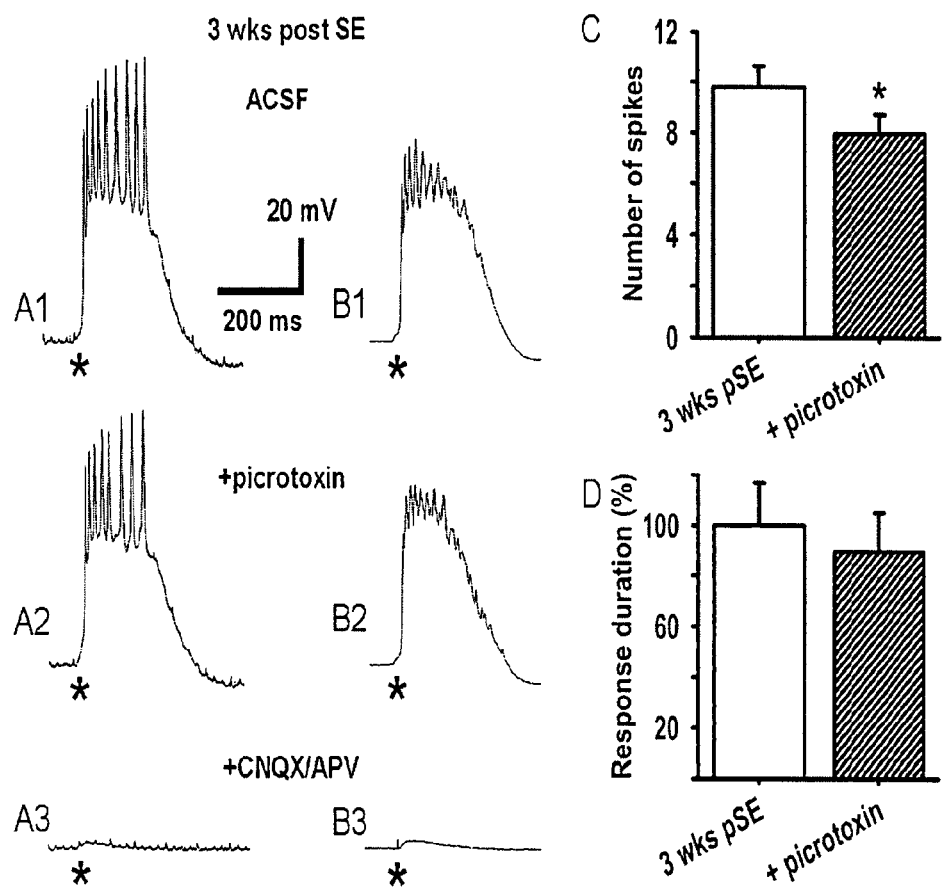
FIG. 11 illustrates that Picrotoxin has a minor effect on polysynaptic bursting, as determined in the experiment(s) of Example 9.

FIG. 11. Picrotoxin has a minor effect on polysynaptic bursting. A: Block of $GABA_A$ receptors by picrotoxin (100 μM) decreased action potential firing during the polysynaptic burst response by a small but significant amount (A1, A2; stimulus 100 nA, 70 μs delivered at *). Subsequent additional block of ionotropic glutamate receptors by CNQX (10 μM) and APV (50 μM) nearly eliminated all postsynaptic responses (A3). B: Averages of 10 bursts from the same cell reveal a shorter burst duration in picrotoxin. Decreased spike amplitudes in these averages indicate reduced precision in the firing pattern during the burst in picrotoxin. C: Population data showing that picrotoxin reduces the mean number of spikes in polysynaptic burst responses from 9.8±0.8 to 7.9±0.7 spikes per response (mean±SEM, n=8 cells, 5 rats, *p<0.05). D: In picrotoxin there is a trend towards a 10.5% decrease of the duration of polysynaptic bursts (mean±SEM, n=8, p=0.094).

Further details of FIG. 12-14, and the experiment(s) which yielded the data reflected in that figure, are as follows.

Figure 12:
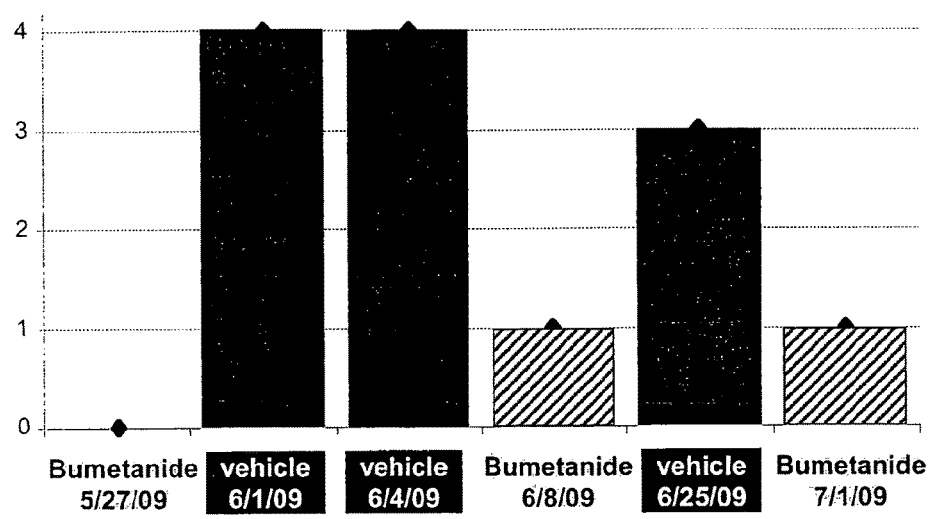
FIG. 12 illustrates the suppression of seizures by bumetanide (0.2 mg/kg body weight, i.p.) 12-17 weeks after Li-pilocarpine SE (n=5 rats). Five Li-pilocarpine SE rats were subjected to a sequence of bumetanide or vehicle injections (5% ethanol in physiological saline, i.p., dates given on bottom line), and seizures occurring in the following 8 hours were analyzed by video recordings. One and the same rat showed seizures after the $2^{nd}$ and $3^{rd}$ bumetanide application, probably due to secondary, downstream changes in this rat enabling spontaneous occurrence of seizures, even when bumetanide has largely normalized Cl and IPSP reversal potential.

FIG. 12 illustrates the suppression of seizures by bumetanide (0.2 mg/kg body weight, i.p.) 12-17 weeks after Li-pilocarpine SE (n=5 rats). Five Li-pilocarpine SE rats were subjected to a sequence of bumetanide or vehicle injections (5% ethanol in physiological saline, i.p., dates given on bottom line), and seizures occurring in the following 8 hours were analyzed by video recordings. One and the same rat showed seizures after the $2^{nd}$ and $3^{rd}$ bumetanide application, probably due to secondary, downstream changes in this rat enabling spontaneous occurrence of seizures, even when bumetanide has largely normalized Cl and IPSP reversal potential.

Figure 13:
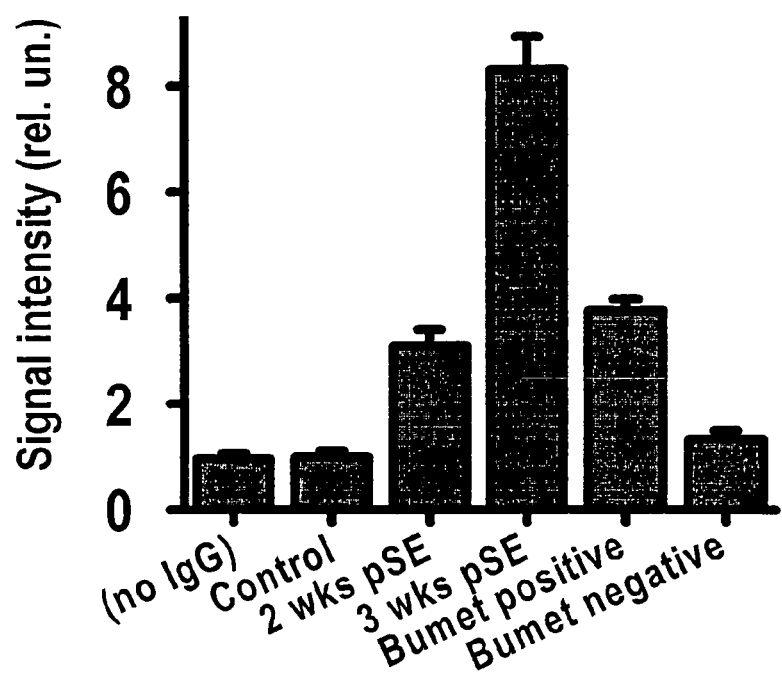
FIG. 13 illustrates that NKCC1 protein shows recovery towards normal adult levels. The plot shows an immunofluorescence signal for NKCC1 protein in deep medial EC without antibody (no IgG), and with antibody in control rats (Control), in SE rats 2, 3 and 17 weeks post SE (wks pSE). 17 weeks post SE NKCC1 signal has recovered to <50% of levels 3 wks pSE in rats in which bumetanide completely prevented SRS (Bumet positive), and >95% in the rat in which bumetanide had become ineffective in preventing SRS (Bumet negative).

FIG. 13 illustrates that NKCC1 protein shows recovery towards normal adult levels. The plot shows an immunofluorescence signal for NKCC1 protein in deep medial EC without antibody (no IgG), and with antibody in control rats (Control), in SE rats 2 and 3 weeks post SE (wks pSE). 17 weeks post SE NKCC1 signal has recovered to <50% of levels 3 wks pSE in rats in which bumetanide completely prevented SRS (Bumet positive), and >95% in the rat in which bumetanide had become ineffective in preventing SRS (Bumet negative).

Figure 14:
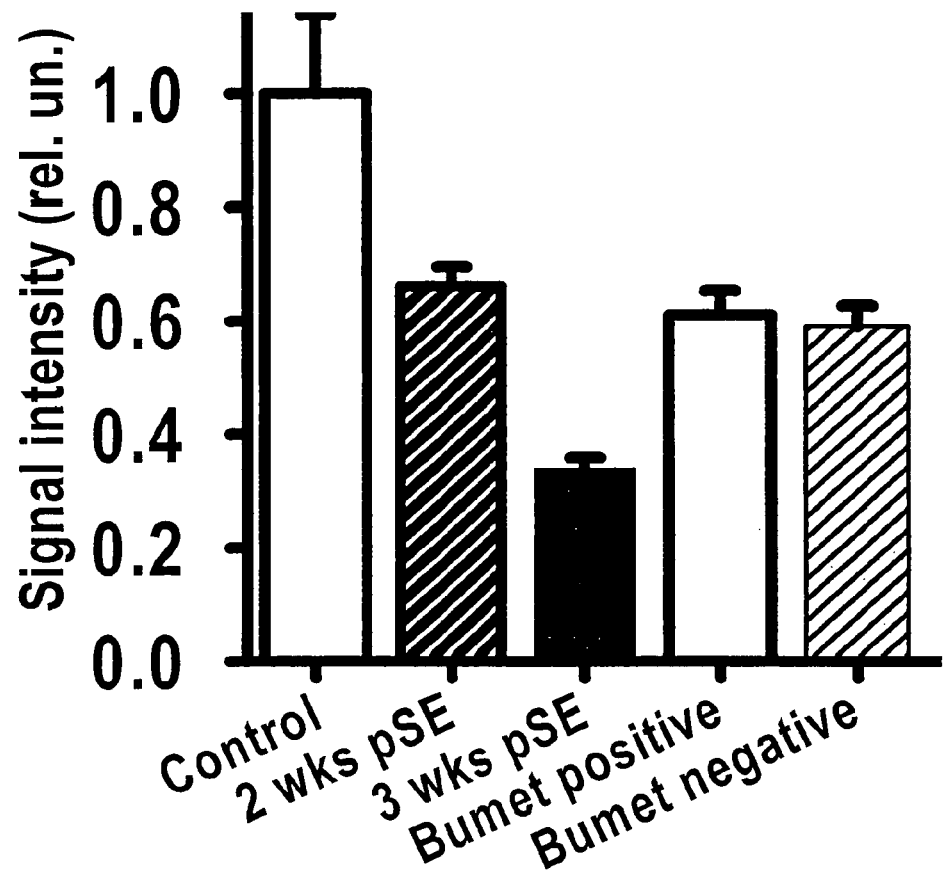
FIG. 14 illustrates that KCC2 protein also shows recovery towards normal adult levels. Immunofluorescence signal for KCC2 protein in deep medial EC in control rats (Control), in SE rats 2 and 3 weeks post SE (wks pSE), and 17 weeks post SE. 17 weeks post SE KCC2 signal has recovered from levels 3 weeks post SE towards normal levels (Bumet positive=rats in which bumetanide completely prevented SRS, and "Bumet negative"=the rat in which bumetanide had become ineffective in preventing SRS).

FIG. 14 illustrates that KCC2 protein also shows recovery towards normal adult levels. Immunofluorescence signal for KCC2 protein in deep medial EC in control rats (Control), in SE rats 2 and 3 weeks post SE (wks pSE), and 17 weeks post SE. 17 weeks post SE KCC2 signal has recovered from levels 3 weeks post SE towards normal levels (Bumet positive=rats in which bumetanide completely prevented SRS, and "Bumet negative"=the rat in which bumetanide had become ineffective in preventing SRS).

New NKCC1 protein data for the rats whose seizure activity after bumetanide or vehicle administration has been quantified in FIG. 12 are presented in FIG. 13, that includes previous NKCC1 data for comparison. Control measurements without antibody (no IgG) further demonstrate that NKCC1 protein levels in control rats are extremely low to zero. 17 weeks after SE NKCC1 protein levels had significantly recovered towards normal levels in rats in which bumetanide administration had prevented spontaneously recurring seizures (SRS, Bumet positive). In the single rat that showed seizures after the $2^{nd}$ and $3^{rd}$ bumetanide administration (about 4 weeks apart on Jun. 8, 2009 and Jul. 1, 2009) NKCC1 had even almost completely normalized.

FIG. 14 shows that KCC2 protein levels also had recovered towards normal adult levels 17 weeks post SE. These data confirm our hypothesis that both, NKCC1 and KCC2 $Cl^-$ transporter expression will normalize over longer time, thus leading to a normalization of distribution and synaptic inhibition with respect to the $Cl^-$ dependent IPSP reversal potential.

Figure 15:
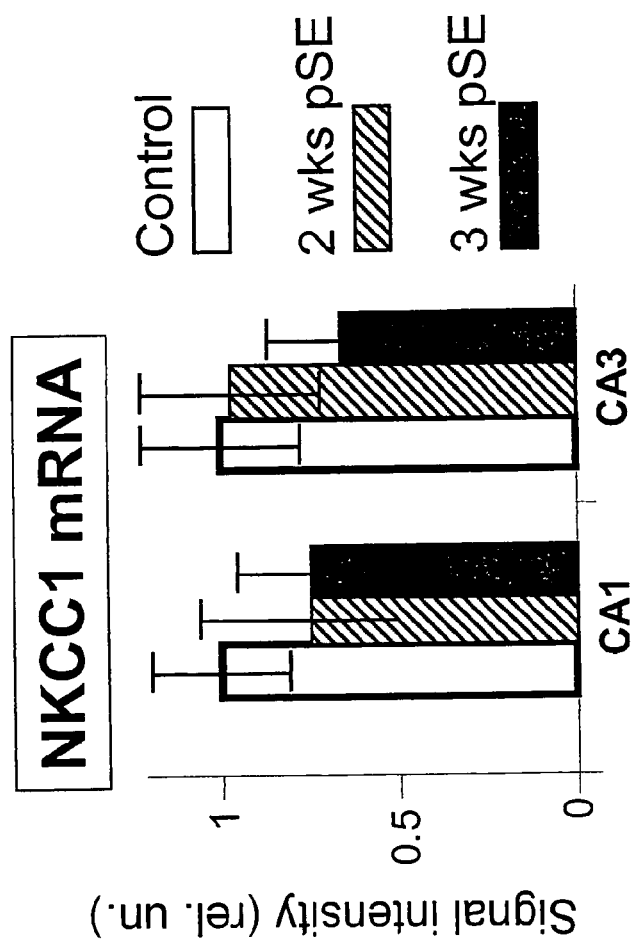
FIG. 15 illustrates that mRNA for NKCC1 does not change in hippocampal pyramidal cell layers CA1 or CA3.

FIG. 15 illustrates that in hippocampal pyramidal cell layers CA1 or CA3 mRNA for NKCC1 does not change 2 and 3 weeks post SE. Bar graph showing that there were no significant changes in NKCC1 mRNA in hippocampal cell layers CA1 and CA3 2 and 3 weeks post SE (2 and 3 wks pSE). Fluorescence in-situ-hybridization data for NKCC1 mRNA extracted from high magnification images of the same tissue used for FIG. 8.

Figure 16:
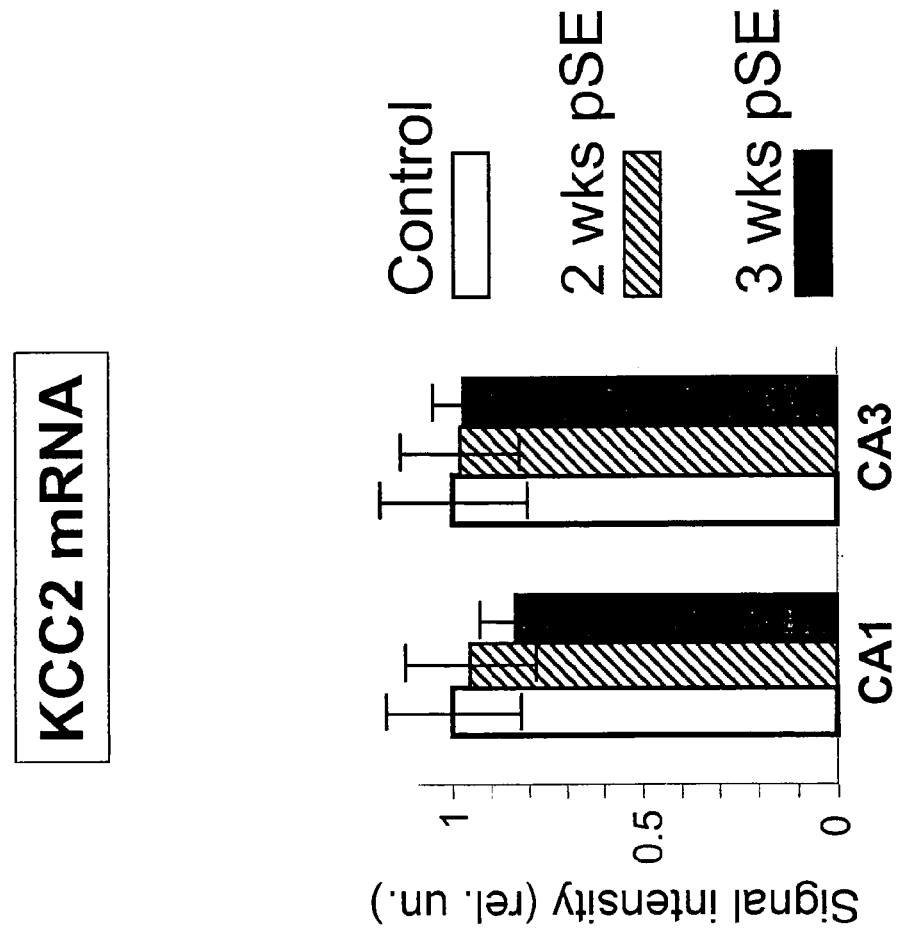
FIG. 16 illustrates that mRNA for KCC2 does not change in hippocampal pyramidal cell layers CA1 or CA3.

FIG. 16 illustrates that mRNA for KCC2 does not change in hippocampal pyramidal cell layers CA1 or CA3. Bar graph showing that there were no significant changes in KCC2 mRNA in hippocampal cell layers CA1 and CA3 2 and 3 weeks post SE (2 and 3 wks pSE). Fluorescence in-situ-hybridization data for NKCC1 mRNA extracted from high magnification images of the same tissue used for FIG. 9.

Figure 17:
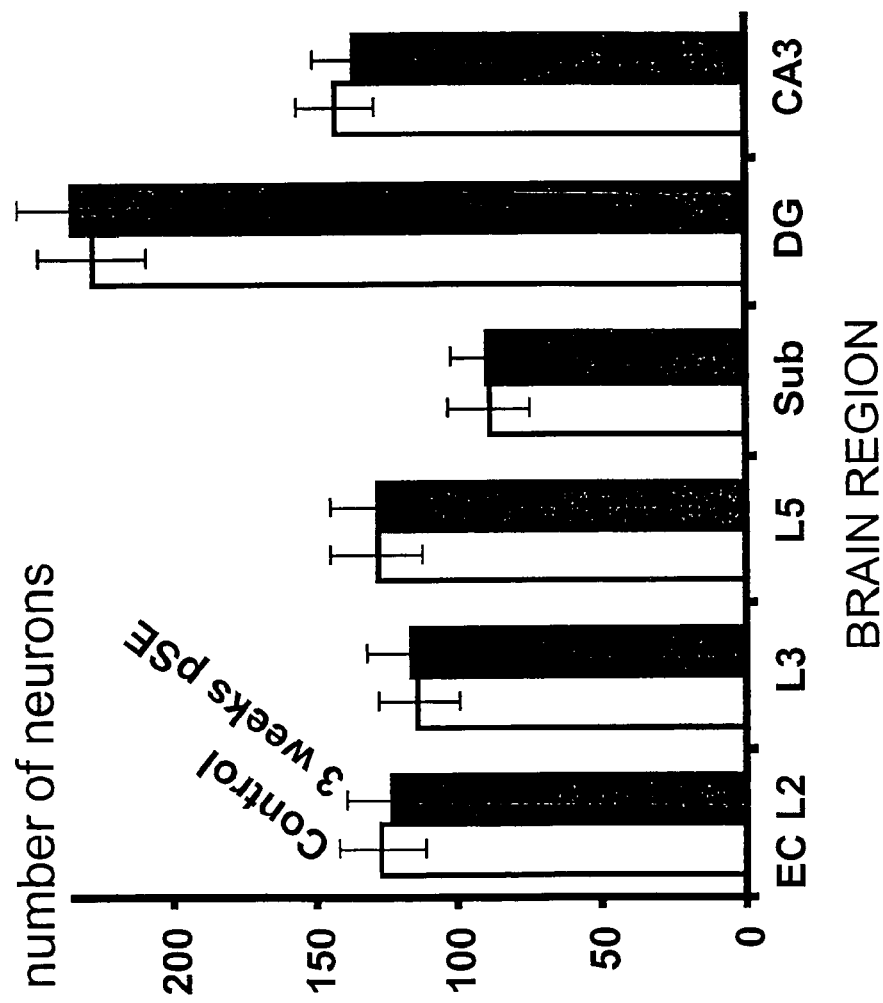
FIG. 17 illustrates that there is no loss of EC L2, L3 or L5 neurons 3 weeks post SE.

FIG. 17: Bar graph showing that 3 weeks post SE there were no significant changes in number of neurons stained with neuron-specific stain "NeuroTrace", neither in EC layer 2 (L2), nor L3, nor L5 (number of neurons/100 μm×100 μm field).

Figure 18:
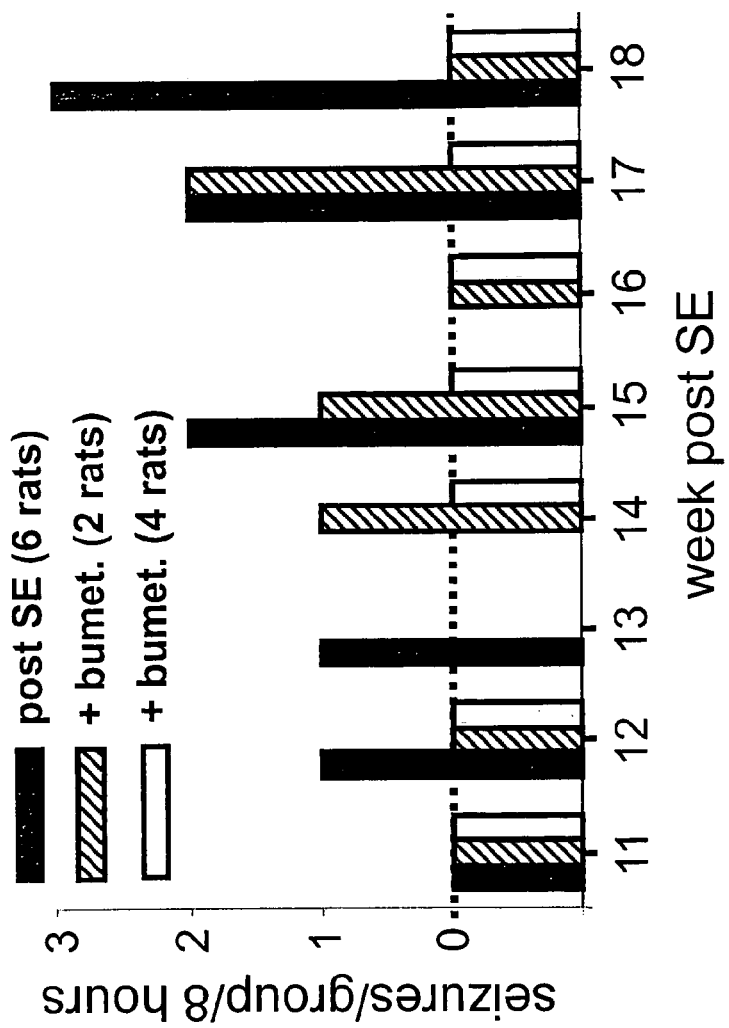
FIG. 18 illustrates occurrence of seizures over time without and with bumetanide treatment.

FIG. 18 illustrates that chronic bumetanide treatment strongly inhibits occurrence of seizures during the chronic period. Plot of seizure occurrence/8 hour video recording vs. week post SE in untreated rats (black bars, water consumption mean±s.d.=29±6.3 ml water/day), and rats treated with bumetanide (bumet.) via the drinking water (mean±s.d.=0.65±0.13 mg bumetanide/day; 32±6.4 ml water/day; dotted and dashed lines). In 4 rats bumetanide prevented seizures completely (open bars), whereas in the two other rats occurrence of seizures, and its progression with time post SE, were both reduced (hatched bars).

Figure 19:
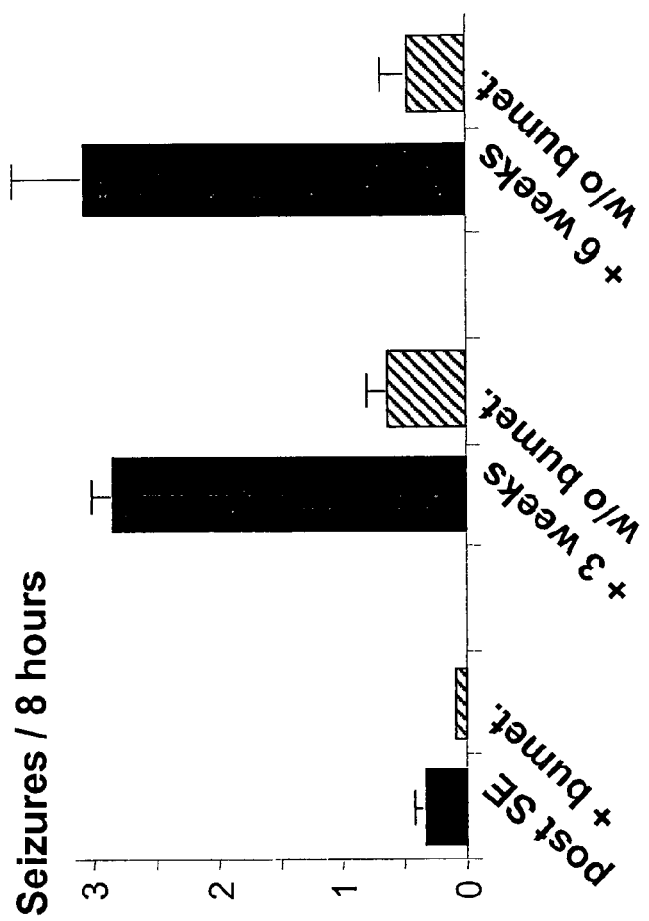
FIG. 19 illustrates inhibition of spontaneous seizures during and 6 weeks beyond chronic bumetanide treatment.

FIG. 19: Chronic bumetanide treatment starting with the $2^{nd}$ week post SE and continued for 20 weeks strongly inhibits occurrence of seizures during and at least 6 weeks beyond end of bumetanide treatment. Bar graph showing the number of seizures occurring on average per rat per 8 hour video recording session during weeks 11-21 post SE (left bar pair), either in untreated rats (black) or treated from the second week post SE chronically for 20 weeks with bumetanide administered via the drinking water (hatched bar). Bumetanide treatment was then ended, and three and six weeks later seizure occurrence in untreated rats had reached a level of about 3 seizures/8 hour recording (black bars, 3 recording sessions per rat), whereas in the previously bumetanide-treated rats seizure occurrence remained much lower (hatched bars, i.e. at 15-22% of seizures occurring in the time post SE-matched control SE rats (n=6 rats in each group).

Figure 20:
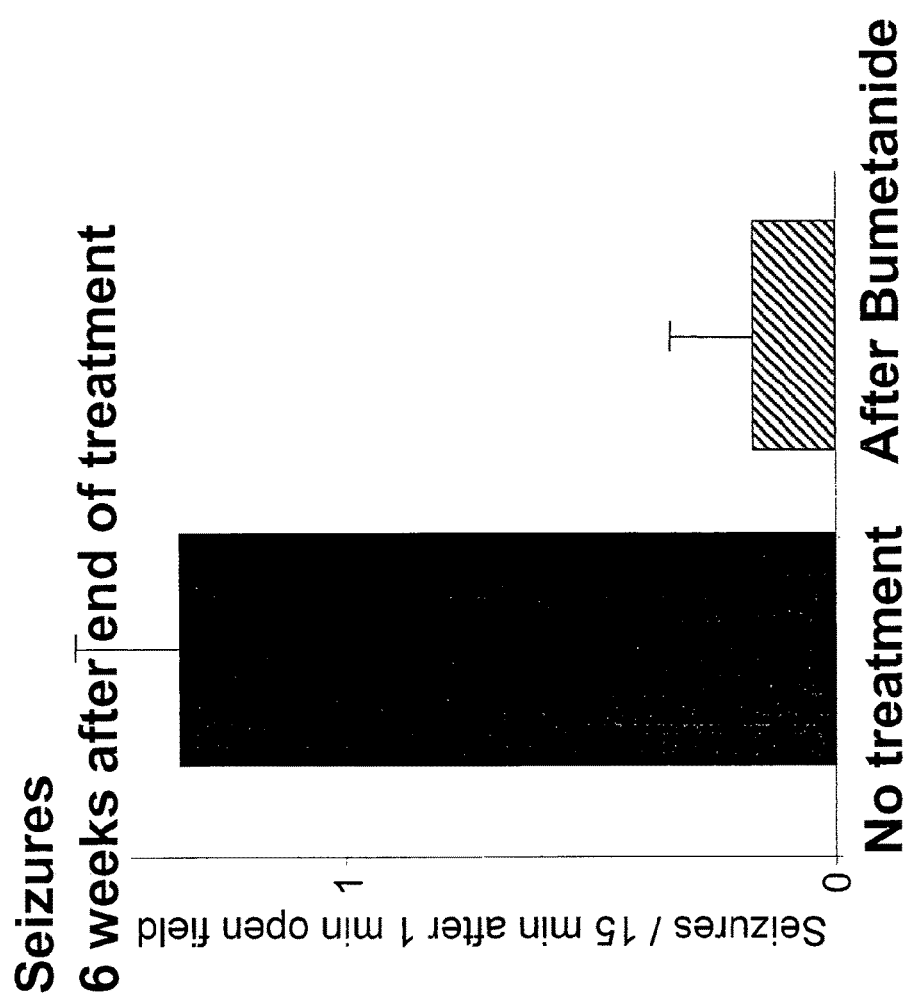
FIG. 20 illustrates suppression of provoked seizures 6 weeks after end of bumetanide treatment.

FIG. 20 illustrates that chronic bumetanide treatment starting 1 week post SE strongly inhibits occurrence of seizures provoked by open field exposure at least 6 weeks beyond end of bumetanide treatment. Bar graph showing the number of seizures occurring within 15 min beginning 1 min after a pilocarpine SE rat, 27 weeks post SE insult, was placed in the center of an open field (1.4×1.4 m), either not treated (black bar) or treated from the second week post SE for 21 weeks chronically with bumetanide via the drinking water (hatched bar). Even 6 weeks after end of bumetanide treatment the treated rats show less than 15% of seizures occurring in the time post SE-matched control SE rats in this test (n=6 rats in each group).

Figure 21:
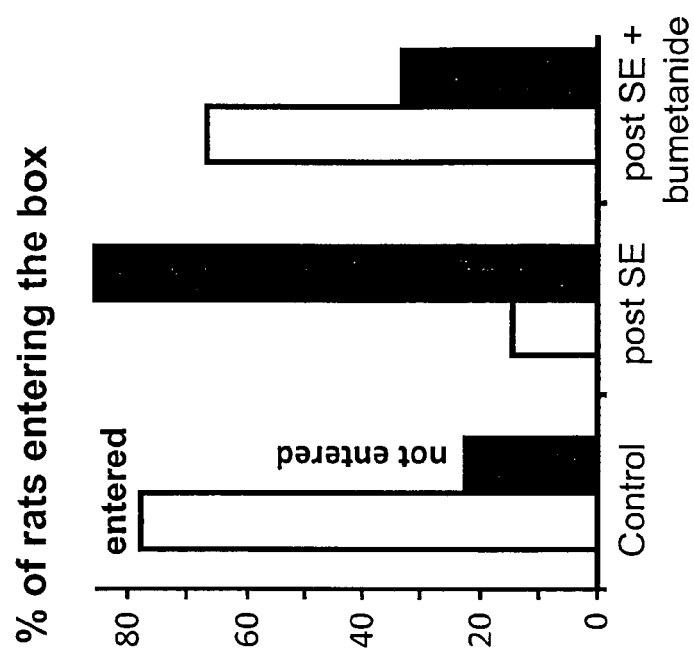
FIG. 21 illustrates recovery of a rat behavior with bumetanide treatment

FIG. 21 illustrates that chronic bumetanide treatment from day 16 post SE for 12 weeks recovers rat behavior entering-a-dark box in an open field. Rats were positioned in the center of an open field (1.4×1.4 m) containing a box, dark on the inside, 0.2(l)×0.3(w)×0.15(h) m, open on one 0.3 m side), placed halfway between the center of the open field and the limiting wall. Behavior was video recorded for 1 min (3 trials/rat, 6 rats in each group). Control rats mostly entered the box and stayed in the box (78% of trials). In contrast, post SE rats (14-15 weeks post SE) mostly ignored the box and did not enter (15% of trials, 7 rats). Bumetanide treated rats from the same SE groups showed behavior similar to the control rats and mostly entered the box (67% of trials, 8 rats).

Figure 22:
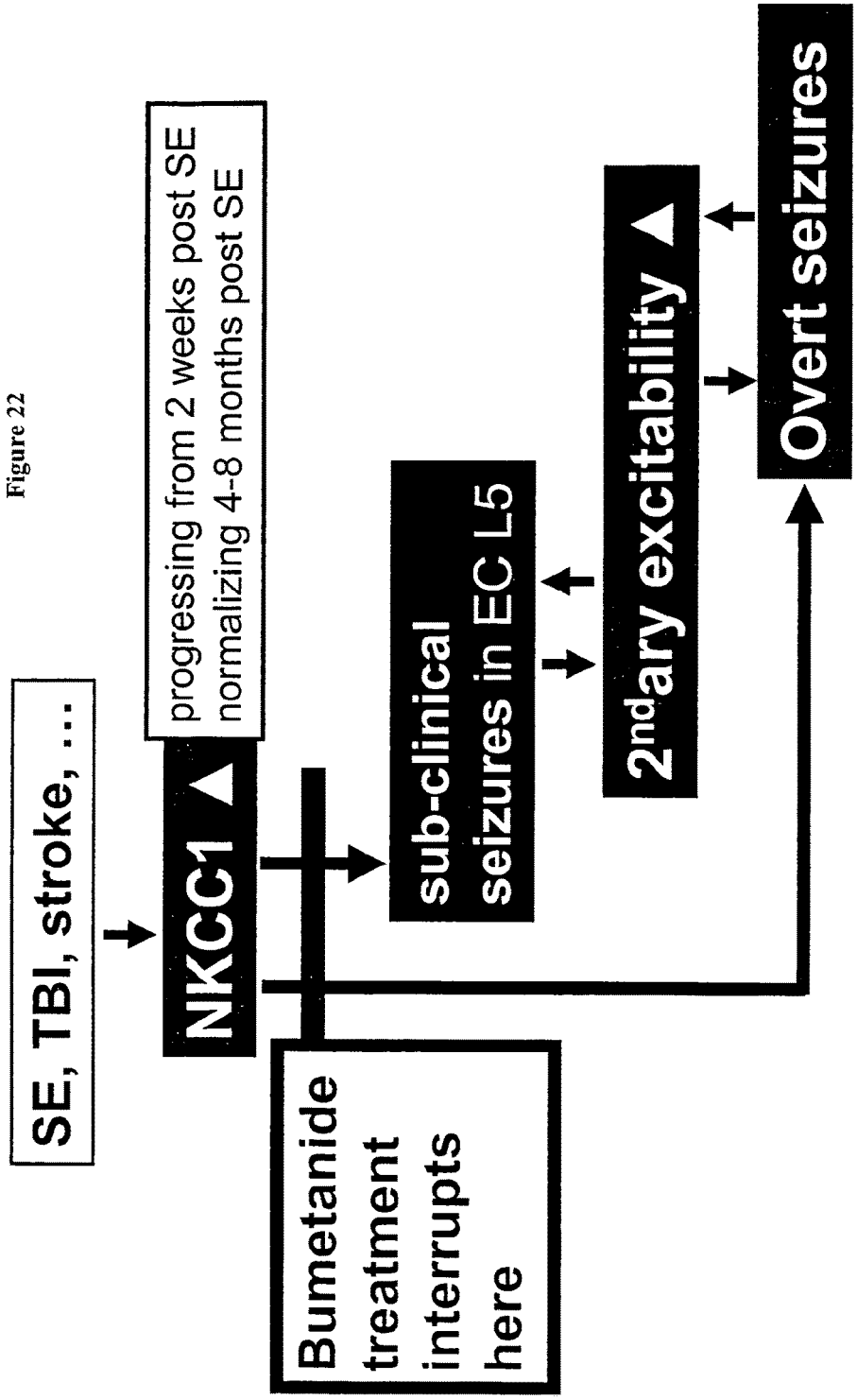
FIG. 22 illustrates our rationale of TLE development, and its prevention by this invention.

FIG. 22 illustrates our rationale of TLE development, and our novel prophylactic and anti-epileptic chronic bumetanide treatment. A TLE-precipitating insult, e.g. SE, traumatic brain injury (TBI), stroke, etc., induces a pathologic re-expression of NKCC1 that progresses during the latent period (2 and 3 weeks post SE). The progressive loss of $GABA_A$-receptor dependent synaptic inhibition leads to epileptiform activity/sub-clinical seizures in EC layer 5 (cf. FIG. 1). This epileptiform activity triggers downstream plastic changes in the EC and downstream brain regions, leading to secondary changes increasing excitability. With progression of changes increasing excitability the likelihood of overt seizures increases. Overt seizures will also trigger downstream plastic changes that further increase brain excitability, leading to a progression of seizure occurrence (demonstrated in FIGS. 18 & 19). Eventually seizures will become independent of NKCC1 activity, and will continue even when NKCC1 normalizes (FIGS. 12 & 13). Bumetanide treatment will restore lower intracellular levels and more efficient inhibition (FIG. 10 A,B), suppressing epileptiform activity during the latent period (FIG. 10 C,D), and seizures during the chronic period (FIGS. 12, 18, 19, 20). Treatment of sub-clinical and overt seizures with bumetanide prevents downstream pathologic changes, leading to normalization of seizure incidence lasting at least 6 weeks beyond treatment (FIGS. 19, 20) and tested behavior (FIG. 21).

Discussion of Experimental Results

Epileptiform neuronal activity during seizures is observed in many brain areas, but its origins following status epilepticus (SE) are unclear. We have used the Li-low dose pilocarpine rat model of temporal lobe epilepsy (TLE) to examine early development of epileptiform activity in the deep entorhinal cortex (EC). We showed that during the 3 week latent period that follows SE, an increasing percentage of neurons in EC layer 5 respond to a single synaptic stimulus with polysynaptic burst depolarizations. This change is paralleled by a progressive depolarizing shift of the IPSP reversal potential in layer 5 neurons, apparently caused by upregulation of the Cl$^-$ inward transporter NKCC1 and concurrent downregulation of the Cl$^-$ outward transporter KCC2, both changes favoring intracellular Cl$^-$ accumulation. Inhibiting Cl$^-$ uptake in the latent period restored more negative GABAergic reversal potentials and eliminated polysynaptic bursts. The changes in the Cl$^-$ transporters were highly specific to the deep entorhinal cortex. They did not occur in layers 1-3, perirhinal cortex, subiculum or dentate gyrus during this period. We propose that the changes in Cl$^-$ homeostasis facilitate hyperexcitability in the deep entorhinal cortex leading to epileptiform discharge there, which subsequently affects downstream cortical regions.

Thus, we have demonstrated the early development of greatly increased excitability in the deep EC, i.e. during the latent period post SE. Neurons in L5 begin to respond to normally subthreshold synaptic stimuli with polysynaptic burst discharge. Moreover, we showed that, during this latent period, a large depolarizing shift of the GABA$_A$ receptor reversal potential occurs due to altered expression of the Cl$^-$ transporters NKCC1 (inward) and KCC2 (outward). These changes in transporter expression occur only in the deep EC, but not adjacent hippocampal and cortical areas, during this early stage of epilepsy development. The direct connection between alterations in Cl$^-$ transport activity and increased polysynaptic bursting is supported by the finding that block of NKCC1 by bumetanide largely restored IPSP reversal potential and greatly reduced polysynaptic burst discharge. Our results implicate ECL5 as an important locus in the development of TLE.

Consequently, the experimental results shown above indicate that in the latent period post SE, prior to occurrence of behavioral seizures, there is a strong increase in neuronal excitability in the deep medial EC, i.e. a progressive increase in the percentage of EC L5 neurons that respond to weak synaptic stimulation with polysynaptic burst discharge. Natural activity patterns in the EC become therefore more and more likely to trigger a spontaneous seizure that by definition will end the latent period. Our findings suggest that after SE, TLE develops primarily in the deep EC. To the best of our knowledge there has been no other study demonstrating epileptiform activity in response to synaptic stimulation in any other brain region during the latent period. This regional specificity is corroborated by the specificity of changes in NKCC1 and KCC2 expression for the deep EC which would lead to disinhibition. The several other cortical and hippocampal regions examined did not show any changes, although latent period interictal activity has been shown in-vivo for CA1 in the high-dose pilocarpine model of TLE (El-Hassar et al., 2007). It is very important that the changes in L5 neuron excitability we have reported occurred without appreciable loss of EC L3 pyramidal neuron loss. A high degree of loss of L3 pyramidal neurons has been shown to be typical of the pathology of late TLE (Du et al., 1993; Du et al., 1995), and can occur within 24 hours of prolonged SE (Du et al., 1995), but these findings are not relevant here since appreciable loss does not occur.

Our protocol for generating SE may be considered to be somewhat weaker than that of Andre et al (Andre et al., 2007) in that Diazepam is administered 1 hr after SE onset rather than 2 hr, plus administration of atropine. Even though neither Diazepam nor atropine stop SE immediately at either time point, we found that this alteration facilitated recovery of rats and produced brain slices with better viability. Rightly or wrongly, we also reasoned that a weaker initial insult might produce more gradually developing cellular or network changes and therefore be easier to analyze. When tested by video monitoring, our protocol produced demonstrable seizure activity in all rats with a latent period of up to 18 weeks (mean=12.7 weeks, see Materials and Methods). Importantly, these latent period durations very well match the latent periods reported for patients (Annegers et al., 1980). This is an important improvement over published rodent TLE models in which the latent period lasts on average only 1-4 weeks, mostly less than 2 weeks (Dube et al., 2000a; Arzimanoglou et al., 2002; Curia et al., 2008; Li et al., 2008). The much shorter latent periods indicate a more severe insult that presumably activates additional or altogether other mechanisms facilitating seizures, but that are apparently mostly not relevant in patients. Thus, Li et al. (Li et al., 2008), using an unusual insult of lithium combined with a high dose of pilocarpine in mice (not an established TLE model) have shown an acute re-expression of NKCC1 in hippocampal region CA1 that lasts into the period studied here. This finding is in contrast to the absence of NKCC1 changes in CA1 in our rats. The cellular changes in EC layer 5 demonstrated by us will most likely be triggered also by the stronger Li-pilocarpine SE and other protocols.

The change in EC L5 excitability is concurrent with, and we propose aided by, a strong and progressive depolarizing shift in the GABA$_A$ergic PSP reversal potential which occurs in about 80% of EC L5 neurons. This percentage is in excellent agreement with the upregulation of the Cl$^-$ F inward transporter NKCC1. The concurrent downregulation of the Cl$^-$ outward transporter KCC2 in most EC L5 neurons will facilitate net Cl$^-$ accumulation by NKCC1, but will not bring by itself E$_{Cl}$ positive to resting membrane potential. The ongoing changes in NKCC1 and KCC2 are also in excellent agreement with the strongly shifted E$_{(PSP)}$ at 3 weeks post SE, even though determination of the latter is less precise, thus adding measurement variability, due to the extrapolation of PSP amplitudes and the reduced difference in slopes.

Weaker shifts in the GABAergic PSP reversal potential have been observed at a much later stage of TLE disease progression; i.e., in late chronic epilepsy in subicular neurons, apparently due to much weaker changes in NKCC1 expression (Cohen et al., 2002; de Guzman et al., 2006; Palma et al., 2006; Huberfeld et al., 2007; Munoz et al., 2007; Sen et al., 2007). The differences in region, stage of disease progression, level of interictal and ictal activity, and expression levels suggest fundamental differences in the signaling network that initiate and further control changed expression levels of NKCC1 and KCC2 in the latent period vs. late chronic TLE.

It has been shown more recently that massive insults can lead to an acute, over 45 days partially recovering re-expression of NKCC1 in the hippocampus, and occurrence of SRS within 2 weeks post insult (Kang et al., 2002; Li et al., 2008). However, it has not been demonstrated in these mice, and is therefore unclear whether 1) NKCC1 has been re-expressed by neurons or glial cells, 2) $GABA_A$-PSP reversal potential is shifted; 3) there is epileptiform activity during the latent period; 4) seizures depend on NKCC1 activity. To the contrary, a most recent study based on one of these studies (Li et al., 2008) demonstrates a complete failure of bumetanide treatment, even with infusion of very high doses, in suppressing SRS (Brandt et al., 2010). Brandt et al. discuss possible reasons for this outcome: "The lack of any significant antiepileptogenic activity of prophylactic treatment with bumetanide in the adult rat TLE model used in the present study may have several reasons, including that (1) the pharmacokinetic problems (rapid elimination, poor brain penetration) associated with systemic administration of bumetanide do not allow to reach and maintain sufficiently high brain concentrations of this drug, (2) alterations in NKCC1 are not critically involved in pilocarpine-induced epileptogenesis, or (3) the time window used for prophylactic treatment in this model, i.e., the first 2 weeks after SE, was not adequate". Suppression of seizures in our data with a low dose of bumetanide shows that pharmacokinetic problems can not underlie failure of the Brandt et al. treatment of seizures (Brandt et al., 2010). Our data indicate that in the first 2 weeks after SE alterations in NKCC1 are not critically involved in epileptogenesis. Thus, also the time window is wrong. In addition, recovering NKCC1 levels cannot underlie beginning occurrence of seizures at the end of the latent period (Li et al., 2008). This mouse model not only shows a much shorter latent period (Li et al., 2008) than what is observed in patients (see above), but also the shown NKCC1 expression in CA1 is in conflict with our data (Kang et al., 2002; Li et al., 2008). Both these facts indicate that the SE models used are not realistic models of TLE (see above). The novelty of our invention is reflected in 1) a realistic match of the latent period by our improved rat TLE model, 2) both, progressing re-expression of NKCC1 and shift of IPSP reversal potential in neurons during the latent period, and 3) effective inhibition by bumetanide of epileptiform activity and seizures during the latent and chronic periods (three to eighteen weeks post SE) as well as 4) at least 6 weeks beyond the end of prolonged bumetanide treatment.

Normal reversal potentials for GABA-PSP's in EC L5 neurons, i.e. ~Vrest, have been found in two distinct SE-TLE models during chronic epilepsy (Fountain et al., 1998; de Guzman et al., 2006), supporting that the very large shifts in $GABA_A$ $E_{(PSP)}$ we report largely recover once chronic epilepsy has been established. There are also other possible explanations: first, recordings may have been obtained from the lateral EC, where we found only small changes in NKCC1 and KCC2. Furthermore, different TLE models were used. De Guzman et al. (2006) studied the high dose pilocarpine rat model of TLE that has been shown to differ significantly from the Li-pilocarpine rat model in the underlying signal transduction pathways that are activated during SE (Ormandy et al., 1989), and also by a much shorter latent period (<2 weeks) and differences in L3 neuronal loss (above). The latter two differences indicate a more severe insult (see above). This could make a difference in the $E_{(PSP)}$ shift as well as whether it recovers in chronic epilepsy or not. We are planning to investigate some of these important issues in future studies.

The inference that the strong depolarizing shift in the $GABA_A$ergic PSP is the primary cause for the observed change in deep EC excitability is supported by the effects of bumetanide, a blocker of the Cl⁻ inward transporter NKCC1. Bumetanide restored a more hyperpolarized PSP reversal potential and largely eliminated epileptiform burst responses to stimulation. These findings demonstrate the necessity for a strongly depolarized $E_{(PSP)}$ for the occurrence of the epileptiform burst responses in this phase post SE, but do not exclude the possibility that other concurrent changes, e.g. the observed reduction in the input conductance of L5 neurons, are required, in addition. The effects of bumetanide further demonstrate that, 3 weeks after SE, inhibition can still be very effective despite the observed decrease in the GABA-PSP conductance that may be due to downregulation of $GABA_AR$ genes or loss of inhibitory synapses and interneurons (Bernard et al., 2004; Goner et al., 2006; Kumar and Buckmaster, 2006). The GABA-PSP has been already slightly depolarizing in control neurons, and, 3 weeks post SE, bumetanide did not fully restore it to that level. Thus, inhibition would be always "shunting", as opposed to "hyperpolarizing". One should keep in mind, however, that for preventing triggering of AP firing by excitatory currents the most important parameter appears to be the amplitude of inhibitory currents at membrane potentials close to the firing threshold. This current amplitude gradually varies with a shift in $E_{(PSP)}$ according to the driving force for Cl⁻ close to the firing threshold (~–45 mV). Hence 3 weeks after SE and in the presence of bumetanide ($E_{(PSP)}$≈–60 mV) the driving force at –45 mV is ~15 mV, as opposed to ~26 mV in control rats, and thus reduced by ~42%. In consequence Cl⁻ currents in this critical membrane potential region are attenuated by both, a decrease in driving force and in GABA-PSP conductance, but, in the presence of bumetanide, are still quite effective to suppress epileptiform activity. This gives hope that largely restoring the Cl⁻-gradient may have therapeutic benefits in-vivo. Our rationale for epileptogenesis, and therapeutic and prophylactic interference with inhibition of NKCC1 activity, is summarized in FIG. 22. The demonstrated very effective inhibition of seizures during and beyond bumetanide treatment beginning in the latent period provides a proof of principle. Furthermore, both, the normalization of an early and highly specific pathologic NKCC1 activity, and the normalization of some altered behavior by this treatment indicate that the proposed anti-epileptic therapy with bumetanide may have the important additional benefit of avoiding at least some of the side effects of current anti-epileptic drugs on intelligence and brain performance.

We believe that our findings uncover key elements operative in the early development of TLE and emphasize the importance of the deep entorhinal cortex in the origin and progression of changes that lead to the disorder.

Abbreviations.

ACSF, Artificial Cerebro-Spinal Fluid; CA, Cornu Ammonis; DAPI, 4', 6'-diamidino-2-phenylindole; EC, entorhinal cortex; $E_{(PSP)}$, PSP reversal potential;

FISH, fluorescence in-situ hybridization; IPSP, inhibitory postsynaptic potential;

PBS, phosphate buffered saline; PBS-T, PBS containing 0.2% Triton-X-100;

PSP, postsynaptic potential; RMP, resting membrane potential; SE, status epilepticus; TLE, temporal lobe epilepsy.

REFERENCES

Aickin, C. C., Deisz, R. A. & Lux, H. D. (1984) Mechanisms of chloride transport in crayfish stretch receptor neurones and guinea pig vas deferens: implications for inhibition mediated by GABA. *Neurosci Lett*, 47, 239-244.

Andre, V., Dube, C., Francois, J., Leroy, C., Rigoulot, M. A., Roch, C., Namer, I. J. & Nehlig, A. (2007) Pathogenesis and pharmacology of epilepsy in the lithium-pilocarpine model. *Epilepsia*, 48 Suppl 5, 41-47.

Annegers, J. F., Grabow, J. D., Groover, R. V., Laws, E. R., Jr., Elveback, L. R. & Kurland, L. T. (1980) Seizures after head trauma: a population study. *Neurology*, 30, 683-689.

Arzimanoglou, A., Hirsch, E., Nehlig, A., Castelnau, P., Gressens, P. & Pereira de Vasconcelos, A. (2002) Epilepsy and neuroprotection: an illustrated review. *Epileptic Disord*, 4, 173-182.

Beck, J., Lenart, B., Kintner, D. B. & Sun, D. (2003) Na—K—Cl cotransporter contributes to glutamate-mediated excitotoxicity. *J Neurosci*, 23, 5061-5068.

Ben-Ari, Y., Gaiarsa, J. L., Tyzio, R. & Khazipov, R. (2007) GABA: a pioneer transmitter that excites immature neurons and generates primitive oscillations. *Physiol Rev*, 87, 1215-1284.

Bernard, C., Anderson, A., Becker, A., Poolos, N. P., Beck, H. & Johnston, D. (2004) Acquired dendritic channelopathy in temporal lobe epilepsy. *Science*, 305, 532-535.

Bormann, J., Hamill, O. P. & Sakmann, B. (1987) Mechanism of anion permeation through channels gated by glycine and gamma-aminobutyric acid in mouse cultured spinal neurones. *J Physiol*, 385, 243-286.

Brandt, C., Nozadze, M., Heuchert, N., Rattka, M. & Loscher, W. (2010) Disease-modifying effects of phenobarbital and the NKCC1 inhibitor bumetanide in the pilocarpine model of temporal lobe epilepsy. *Neurosci*, 30, 8602-8612.

Cohen, I., Navarro, V., Clemenceau, S., Baulac, M. & Miles, R. (2002) On the origin of interictal activity in human temporal lobe epilepsy in vitro. *Science*, 298, 1418-1421.

Curia, G., Longo, D., Biagini, G., Jones, R. S. & Avoli, M. (2008) The pilocarpine model of temporal lobe epilepsy. *J Neurosci Methods*, 172, 143-157.

de Guzman, P., Inaba, Y., Biagini, G., Baldelli, E., Mollinari, C., Merlo, D. & Avoli, M. (2006) Subiculum network excitability is increased in a rodent model of temporal lobe epilepsy. *Hippocampus*, 16, 843-860.

Delpire, E. (2000) Cation-Chloride Cotransporters in Neuronal Communication. *News Physiol Sci*, 15, 309-312.

Du, F., Eid, T., Lothman, E. W., Kohler, C. & Schwarcz, R. (1995) Preferential neuronal loss in layer III of the medial entorhinal cortex in rat models of temporal lobe epilepsy. *J Neurosci*, 15, 6301-6313.

Du, F., Whetsell, W. O., Abou, K. B., Blumenkopf, B., Lothman, E. W. & Schwarcz, R. (1993) Preferential neuronal loss in layer III of the entorhinal cortex in patients with temporal lobe epilepsy. *Epilepsy Res*, 16, 223-233.

Dube, C., Boyet, S., Marescaux, C. & Nehlig, A. (2000a) Progressive metabolic changes underlying the chronic reorganization of brain circuits during the silent phase of the lithium-pilocarpine model of epilepsy in the immature and adult Rat. *Exp Neurol*, 162, 146-157.

Dube, C., Marescaux, C. & Nehlig, A. (2000b) A metabolic and neuropathological approach to the understanding of plastic changes that occur in the immature and adult rat brain during lithium-pilocarpine-induced epileptogenesis. *Epilepsia*, 41 Suppl 6, S36-43.

Egorov, A. V., Angelova, P. R., Heinemann, U. & Müller, W. (2003) Ca2+-independent muscarinic excitation of rat medial entorhinal cortex layer V neurons. *Eur J Neurosci*, 18, 3343-3351.

Egorov, A. V., Heinemann, U. & Müller, W. (2002) Differential excitability and voltage-dependent Ca2+ signalling in two types of medial entorhinal cortex layer V neurons. *Eur J Neurosci*, 16, 1305-1312.

El-Hassar, L., Milh, M., Wendling, F., Ferrand, N., Esclapez, M. & Bernard, C. (2007) Cell domain-dependent changes in the glutamatergic and GABAergic drives during epileptogenesis in the rat CA1 region. *J Physiol*, 578, 193-211.

Fountain, N. B., Bear, J., Bertram, E. H., 3rd & Lothman, E. W. (1998) Responses of deep entorhinal cortex are epileptiform in an electrogenic rat model of chronic temporal lobe epilepsy. *J Neurophysiol*, 80, 230-240.

Gorter, J. A., van Vliet, E. A., Aronica, E., Breit, T., Rauwerda, H., Lopes da Silva, F. H. & Wadman, W. J. (2006) Potential new antiepileptogenic targets indicated by microarray analysis in a rat model for temporal lobe epilepsy. *J Neurosci*, 26, 11083-11110.

Guzowski, J. F., McNaughton, B. L., Barnes, C. A. & Worley, P. F. (1999) Environment-specific expression of the immediate-early gene Arc in hippocampal neuronal ensembles. *Nat Neurosci*, 2, 1120-1124.

Hamam, B. N., Kennedy, T. E., Alonso, A. & Amaral, D. G. (2000) Morphological and electrophysiological characteristics of layer V neurons of the rat medial entorhinal cortex. *J Comp Neurol*, 418, 457-472.

Hannaert, P., Alvarez-Guerra, M., Pirot, D., Nazaret, C. & Garay, R. P. (2002) Rat NKCC2/NKCC1 cotransporter selectivity for loop diuretic drugs. *Naunyn Schmiedebergs Arch Pharmacol*, 365, 193-199.

Huberfeld, G., Wittner, L., Clemenceau, S., Baulac, M., Kaila, K., Miles, R. & Rivera, C. (2007) Perturbed chloride homeostasis and GABAergic signaling in human temporal lobe epilepsy. *J Neurosci*, 27, 9866-9873.

Kang, T. C., An, S. J., Park, S. K., Hwang, I. K., Yoon, D. K., Shin, H. S. & Won, M. H. (2002) Changes in Na(+)-K(+)-Cl(−) cotransporter immunoreactivity in the gerbil hippocampus following transient ischemia. *Neurosci Res*, 44, 249-254.

Kobayashi, M., Wen, X. & Buckmaster, P. S. (2003) Reduced inhibition and increased output of layer II neurons in the medial entorhinal cortex in a model of temporal lobe epilepsy. *J Neurosci*, 23, 8471-8479.

Kumar, S. S. & Buckmaster, P. S. (2006) Hyperexcitability, interneurons, and loss of GABAergic synapses in entorhinal cortex in a model of temporal lobe epilepsy. *J Neurosci*, 26, 4613-4623.

Li, X., Zhou, J., Chen, Z., Chen, S., Zhu, F. & Zhou, L. (2008) Long-term expressional changes of Na+-K+-Cl-co-transporter 1 (NKCC1) and K+-Cl-co-transporter 2 (KCC2) in CA1 region of hippocampus following lithium-pilocarpine induced status epilepticus (PISE). *Brain Res*, 1221, 141-146.

Misgeld, U., Deisz, R. A., Dodt, H. U. & Lux, H. D. (1986) The role of chloride transport in postsynaptic inhibition of hippocampal neurons. *Science*, 232, 1413-1415.

Munoz, A., Mendez, P., DeFelipe, J. & Alvarez-Lee inans, F. J. (2007) Cation-chloride cotransporters and GABA-ergic innervation in the human epileptic hippocampus. *Epilepsia*, 48, 663-673.

Ormandy, G. C., Jope, R. S. & Snead, O. C., 3rd (1989) Anticonvulsant actions of MK-801 on the lithium-pilocarpine model of status epilepticus in rats. *Exp Neurol*, 106, 172-180.

Palma, E., Amici, M., Sobrero, F., Spinelli, G., Di Angelantonio, S., Ragozzino, D., Mascia, A., Scoppetta, C., Esposito, V., Miledi, R. & Eusebi, F. (2006) Anomalous levels of Cl— transporters in the hippocampal subiculum from temporal lobe epilepsy patients make GABA excitatory. *Proc Natl Acad Sci USA,* 103, 8465-8468.

Pathak, H. R., Weissinger, F., Terunuma, M., Carlson, G. C., Hsu, F. C., Moss, S. J. & Coulter, D. A. (2007) Disrupted dentate granule cell chloride regulation enhances synaptic excitability during development of temporal lobe epilepsy. *J Neurosci,* 27, 14012-14022.

Payne, J. A., Stevenson, T. J. & Donaldson, L. F. (1996) Molecular characterization of a putative K—Cl cotransporter in rat brain. A neuronal-specific isoform. *J Biol Chem,* 271, 16245-16252.

Peterson, S. L., Purvis, R. S. & Griffith, J. W. (2005) Comparison of neuroprotective effects induced by alpha-phenyl-N-tert-butyl nitrone (PBN) and N-tert-butyl-alpha-(2 sulfophenyl) nitrone (S-PBN) in lithium-pilocarpine status epilepticus. *Neurotoxicology,* 26, 969-979.

Russell, J. M. (2000) Sodium-potassium-chloride cotransport. *Physiol Rev,* 80, 211-276.

Sen, A., Martinian, L., Nikolic, M., Walker, M. C., Thom, M. & Sisodiya, S. M. (2007) Increased NKCC1 expression in refractory human epilepsy. *Epilepsy Res,* 74, 220-227.

Staley, K. J., Soldo, B. L. & Proctor, W. R. (1995) Ionic mechanisms of neuronal excitation by inhibitory GABAA receptors. *Science,* 269, 977-981.

Sung, K. W., Kirby, M., McDonald, M. P., Lovinger, D. M. & Delpire, E. (2000) Abnormal GABAA receptor-mediated currents in dorsal root ganglion neurons isolated from Na—K-2Cl cotransporter null mice. *J Neurosci,* 20, 7531-7538.

Wang, C., Shimizu-Okabe, C., Watanabe, K., Okabe, A., Matsuzaki, H., Ogawa, T., Mori, N., Fukuda, A. & Sato, K. (2002) Developmental changes in KCC1, KCC2, and NKCC1 mRNA expressions in the rat brain. *Brain Res Dev Brain Res,* 139, 59-66.

Yamada, J., Okabe, A., Toyoda, H., Kilb, W., Luhmann, H. J. & Fukuda, A. (2004) Cl-uptake promoting depolarizing GABA actions in immature rat neocortical neurones is mediated by NKCC1. *J Physiol,* 557, 829-841.

What is claimed is:

1. A method of inhibiting or reducing the severity of Mesial temporal lobe epilepsy (TLE) in a subject, the method comprising administering a therapeutically effective amount of a NKCC1 inhibitor to the subject within two to four weeks or eight to twenty-four weeks after the subject has suffered from an insult known to precipitate TLE; wherein said NKCC1 inhibitor is a loop diuretic or a pharmaceutically acceptable salt or ester thereof, or an inhibitor of re-expression of NKCC1, and wherein the inhibitor of re-expression of NKCC1 is not a GABA modulator.

2. The method of claim 1, wherein the insult known to precipitate TLE is selected from the group consisting of status epilepticus (SE), petit mal epilepsy, absence, myoclonic, clonic, tonic, tonic-clonic and atonic seizures, acquired aphasia, acquired aphasia with epilepsy (Landau-Kleffner syndrome), acquired epileptic aphasia, cortical dysplasia-focal epilepsy syndrome (CDFE), neonatal seizures, hippocampal sclerosis (HS) and hippocampal, cerebral, and cerebellar atrophy, febrile seizures including complex febrile convulsions (CFC), traumatic brain injury, stroke, hypoxic-ischemic event, metabolic disorder and brain tumors.

3. The method of claim 1, wherein the NKCC1 inhibitor is administered to the subject during the latent period following the subject's development of status epilepticus (SE).

4. The method of claim 1, wherein the NKCC1 inhibitor is administered to the subject within around eight to around twenty-four weeks after the subject develops SE seizures.

5. The method of claim 1, wherein the NKCC1 inhibitor is administered to the subject within around two to around four weeks after the subject develops SE seizures.

6. The method of claim 1, wherein the NKCC1 inhibitor and a second therapeutic agent are co-administered to the subject after the subject has suffered from an insult known to precipitate TLE, wherein the second therapeutic agent comprises a GABA modulating composition, an anticonvulsant agent, an ion channel inactivator, an antidiuretic agent, or a combination thereof.

7. The method of claim 1, wherein the NKCC1 inhibitor is a loop diuretic selected from the group consisting of torasemide, furosemide, azosemide, bumetanide, piretanide, tripamide, etozoline and its metabolite ozolinone, and cicletanine, and pharmaceutically acceptable salts and esters thereof.

8. The method of claim 6, wherein the GABA-modulating composition is selected from the group consisting of benzodiazepines, Gabapentin, Pregabalin, 4-aminobutanoic acid (GABA), 4-amino-3-(4-chlorophenyl)butanoic acid (baclofen), 4-amino-3-phenylbutanoic acid, 4-amino-3-hydroxybutanoic acid, 4-amino-3-(4-chlorophenyl)-3-hydroxyphenylbutanoic acid, 4-amino-3-(thien-2-yl)butanoic acid, 4-amino-3-(5-chlorothien-2-yl)butanoic acid, 4-amino-3-(5-bromothien-2-yl)butanoic acid, 4-amino-3-(5-methylthien-2-yl)butanoic acid, 4-amino-3-(2-imidazolyl)butanoic acid, 4-guanidino-3-(4-chlorophenyl)butanoic acid, (3-aminopropyl)phosphonous acid, (4-aminobut-2-yl)phosphonous acid, sodium butyrate, (3-amino-2-methylpropyl)phosphonous acid, (3-aminobutyl)phosphonous acid, (3-amino-2-(4-chlorophenyl)propyl)phosphonous acid, (3-amino-2-(4-chlorophenyl)-2-hydroxypropyl)phosphonous acid, (3-amino-2-(4-fluorophenyl)propyl)phosphonous acid, (3-amino-2-phenylpropyl)phosphonous acid, (3-amino-2-hydroxypropyl)phosphonous acid, (E)-(3-aminopropen-1-yl)phosphonous acid, (3-amino-2-cyclohexylpropyl)phosphonous acid, (3-amino-2-benzylpropyl)phosphonous acid, [3-amino-2-(4-methylphenyl)propyl]phosphonous acid, [3-amino-2-(4-trifluoromethylphenyl)propyl]phosphonous acid, [3-amino-2-(4-methoxyphenyl)propyl]phosphonous acid, [3-amino-2-(4-chlorophenyl)-2-hydroxypropyl]phosphonous acid, (3-aminopropyl)methylphosphinic acid, (3-amino-2-hydroxypropyl)methylphosphinic acid, (3-aminopropyl)(difluoromethyl)phosphinic acid, (4-aminobut-2-yl)methylphosphinic acid, (3-amino-1-hydroxypropyl)methylphosphinic acid, (3-amino-2-hydroxypropyl)(difluoromethyl)phosphinic acid, (E)-(3-aminopropen-1-yl)methylphosphinic acid, (3-amino-2-oxo-propyl)methylphosphinic acid, (3-aminopropyl)hydroxymethylphosphinic acid, (5-aminopent-3-yl)methylphosphinic acid, (4-amino-1,1,1-trifluorobut-2-yl)methylphosphinic acid, (3-amino-2-(4-chlorophenyl)propyl)sulfinic acid, and 3-aminopropylsulfinic acid or a mixture thereof.

9. The method of claim 1, wherein the NKCC1 inhibitor is administered chronically to the subject after the subject suffers from recurrent insults known to precipitate TLE.

10. The method of claim 9, wherein the subject suffers from recurrent SE.

11. The method of claim 2, wherein said NKCC1 inhibitor acts via inhibition of NKCC1 activity or via inhibition of re-expression of NKCC1 within 2-4 weeks after said insult.

* * * * *